United States Patent
Noto et al.

(10) Patent No.: US 12,086,735 B2
(45) Date of Patent: *Sep. 10, 2024

(54) LOCAL GENETIC ETHNICITY DETERMINATION SYSTEM

(71) Applicant: Ancestry.com DNA, LLC, Lehi, UT (US)

(72) Inventors: Keith D. Noto, San Francisco, CA (US); Yong Wang, Foster City, CA (US)

(73) Assignee: Ancestry.com DNA, LLC, Lehi, UT (US)

( * ) Notice: Subject to any disclaimer, the term of this patent is extended or adjusted under 35 U.S.C. 154(b) by 1283 days.

This patent is subject to a terminal disclaimer.

(21) Appl. No.: 16/737,269

(22) Filed: Jan. 8, 2020

(65) Prior Publication Data

US 2020/0160202 A1 May 21, 2020

Related U.S. Application Data

(63) Continuation of application No. 15/209,458, filed on Jul. 13, 2016, now Pat. No. 10,558,930.

(60) Provisional application No. 62/191,968, filed on Jul. 13, 2015.

(51) Int. Cl.
| | | |
|---|---|---|
| *G06N 7/01* | (2023.01) | |
| *G06N 20/00* | (2019.01) | |
| *G16B 10/00* | (2019.01) | |
| *G16B 40/00* | (2019.01) | |
| *G16B 40/20* | (2019.01) | |

(52) U.S. Cl.
CPC ............... *G06N 7/01* (2023.01); *G06N 20/00* (2019.01); *G16B 10/00* (2019.02); *G16B 40/20* (2019.02); *G16B 40/00* (2019.02)

(58) Field of Classification Search
CPC ........ G16B 30/00; G16B 20/20; G16B 30/10; G16B 20/00; G16B 40/00; G16B 40/20; G16B 40/30; G16B 45/00; G16B 50/00; G16B 10/00; G16B 5/20; G16B 50/10; G16B 50/30; G16B 50/20; G06N 20/00; G06N 7/01; G06N 5/04; G06N 20/20; G06N 5/01; G06N 5/02; G06N 3/08; G06N 3/09; G06N 5/042; G06N 5/046; G06N 3/047; G06N 3/084; G06N 3/02; G06N 7/00; C12Q 1/6869; C12Q 2600/156; C12Q 2537/165; C12Q 1/6827; C12Q 2600/172; G16H 10/60; G06F 17/18; G06F 16/29; G06F 40/169; G06F 16/9024; G06F 16/9535; G06F 16/2228; G06F 30/27; G06F 16/20; G06F 16/24573; G06F 16/248; G06F 16/583; G06F 16/00; G06T 2200/24; G06T 2207/20081; G06T 11/206; C12N 2320/34; G01N 2800/60; G06V 10/82; G06V 2201/04; G06V 30/1988

See application file for complete search history.

(56) References Cited

U.S. PATENT DOCUMENTS

| | | | |
|---|---|---|---|
| 8,510,057 B1 | 8/2013 | Avey et al. | |
| 9,213,947 B1 | 12/2015 | Do et al. | |
| 9,367,800 B1 * | 6/2016 | Do | G16B 20/00 |
| 9,836,576 B1 | 12/2017 | Do et al. | |
| 9,940,433 B2 * | 4/2018 | Han | G16B 40/00 |
| 10,558,930 B2 * | 2/2020 | Noto | G16B 10/00 |
| 10,692,587 B2 * | 6/2020 | Song | G16B 40/30 |
| 10,720,229 B2 * | 7/2020 | Barber | G06N 5/048 |
| 11,211,149 B2 * | 12/2021 | Curtis | G16B 10/00 |
| 11,232,854 B2 * | 1/2022 | Anderson | G16B 10/00 |
| 2002/0143578 A1 | 10/2002 | Cole et al. | |
| 2003/0113727 A1 | 6/2003 | Girn et al. | |
| 2005/0025508 A1 | 2/2005 | Karakama et al. | |
| 2008/0154566 A1 | 6/2008 | Myres et al. | |
| 2008/0255768 A1 | 10/2008 | Martin et al. | |
| 2013/0085728 A1 | 4/2013 | Tang et al. | |
| 2013/0149707 A1 | 6/2013 | Sorenson et al. | |
| 2013/0163860 A1 | 6/2013 | Suzuki et al. | |
| 2013/0297221 A1 | 11/2013 | Johnson et al. | |
| 2014/0045705 A1 | 2/2014 | Bustaman et al. | |
| 2014/0045708 A1 | 2/2014 | Feng et al. | |
| 2014/0108527 A1 | 4/2014 | Aravanis et al. | |
| 2017/0062577 A1 | 3/2017 | Brewer et al. | |
| 2020/0082909 A1 * | 3/2020 | Wang | G06N 7/01 |

(Continued)

FOREIGN PATENT DOCUMENTS

| | | |
|---|---|---|
| WO | WO 2014/151088 A2 | 9/2014 |
| WO | WO 2015/051006 A2 | 4/2015 |

OTHER PUBLICATIONS

Dilthey, A. (Feb. 2013) Multi-population classical HLA-type imputation. PLOS Computational Biology, vol. 9, issue 2, e1002877 13 pages, and some supplemental information, 17 pages. (Year: 2013).*

(Continued)

*Primary Examiner* — Mary K Zeman
(74) *Attorney, Agent, or Firm* — Fenwick & West LLP

(57) ABSTRACT

An input sample SNP genotype is divided into a plurality of windows, each including a sequence of SNPs. For each window, a diploid hidden Markov Model (HMM) is built and from a haplotype Markov Model (MM). The diploid HMM for a window is used to determine the probability that the window corresponds to a pair of labels (e.g., ethnicity labels). An inter-window HMM, with a set of states for each window, is built based on the diploid HMMs for each window. Labels are assigned to the input sample genotype based on the inter-window HMM.

20 Claims, 7 Drawing Sheets

(56) References Cited

U.S. PATENT DOCUMENTS

2020/0286579 A1* 9/2020 Song .................. G16H 10/60
2021/0134387 A1* 5/2021 McMaster-Schraiber ..................
G06N 3/045

OTHER PUBLICATIONS

Definition of ethnicity, Wikipedia.com downloaded Sep. 2023 (Year: 2023).*
Browning, B.L. et al., "Efficient multilocus association testing for whole genome association studies using localized haplotype clustering," Genetic Epidemiology, Jan. 1, 2007, vol. 31, No. 5, pp. 365-375.
Browning, S.R. et al., "Haplotype phasing: existing methods and new developments," Nature Reviews Genetics, Sep. 16, 2011, vol. 12, No. 10, pp. 703-714.
Browning, S.R. et al., "Rapid and Accurate Haplotype Phasing and Missing-Data Inference for Whole-Genome Association Studies by Use of Localized Haplotype Clustering," American Journal of Human Genetics, Sep. 21, 2007, vol. 81, No. 5, pp. 1084-1097.
Browning, S.R., "Multilocus Association Mapping Using Variable-Length Markov Chains," American Journal of Human Genetics, Apr. 7, 2006, vol. 78, No. 6, pp. 903-913.
Eronen, L. et al., "A Markov chain approach to reconstruction of long haplotypes," Pacific Symposium on Biocomputing, Jan. 1, 2004, 12 pages.
European Patent Office, Extended European Search Report, European Patent Application No. 16823964, Apr. 3, 2019, 14 paqes.
Guan, Y. Detecting Structure of Haplotypes and Local Ancestry. 2014 Genetics, vol. 196, p. 625-642.
Li, Y. et al. Genotype Imputation. 2009. Ann. Rev. Genomics Hum. Genet. vol. 10, p. 387-406.
Purcell, S. et al. PLINK: A Tool Set for Whole-Genome Association and Population-based Linkage Analysis. 2007. The Am J Hum Genet. vol. 81, p. 559-575.
PCT International Search Report and Written Opinion, PCT Application No. PCT/IB2016/054180, Oct. 18, 2016, 11 pages.
Horton, R. et al., "Variation Analysis and Gene Annotation of Eight MHC Haplotypes: the MHC Halotype Project," Immunogenetics, 2008, pp. 1-18, vol. 60.
Dermitzakis, E. T. et al., "The International HapMap 3 Consortium, Integrating common and rare genetic variation in diverse human populations," Nature, Sep. 2010, vol. 467, 8 pages.
Falush, D. et al., "Inference of Population Structure Using Multilocus Genotype Data: Linked Loci and Correlated Allele Frequencies," Genetics Society of America, Mar. 2003, pp. 1567-1587.
Jarvis, J.P. et al., "Patterns of Ancestry, Signatures of Natural Selection, and Genetic Association with Stature in Western African Pygmies," PLoS Genetics, Apr. 2012, vol. 8, No. 4, 15 pages.
Morrison, A. C. et al., "Prediction of Coronary Heart Disease Risk using a Genetic Risk Score: The Atherosclerosis Risk in Communities Study," American Journal of Epidemiology, Apr. 2007, vol. 166, No. 1, 8 pages.
Platt, J.C., "Probabilistic Outputs for Support Vector Machines and Comparisons to Regularized Likelihood Mehotds," Microsoft Research, Mar. 26, 1999, 11 pages.
Price, A.L., "Sensitive Detection of Chromosomal Segments of Distinct Ancestry in Admixed Populations," PLoS Genetics, Jun. 2009, vol. 5, No. 6, pp. 1-18.
Qian, Y. et al., "Efficient clustering of identity-by-descent between multiple individuals," Oxford University Press, 2013, vol. 30, No. 7, pp. 915-922.
Rabiner, L.R., "A Tutorial on Hidden Markov Models and Selected Applications in Speech Recognition," Proceedings of the IEEE, Feb. 1989, vol. 77, No. 2, 30 pages.
Ron, D. et al., "On the Learnability and Usage of Acyclic Probablistic Finite Automata," Journal of Computer and System Sciences, 1998, vol. 56, pp. 133-152.
Scheet, P. et al., "A Fast and Flexible Statistical Model for Large-Scale Population Genotype Data: Applications to Inferring Missing Genotypes and Haplotypic Phase," University of Washington, The American Journal of Human Genetics, Apr. 2006, vol. 78, pp. 628-644.
Seligsohn, U. et al., Genetic Susceptibility to Venous Thrombosis, The New England Journal of Medicine, Apr. 2001, vol. 344, No. 16, pp. 1222-1231.
Staples, J. et al., "PRIMUS: Rapid Reconstruction of Pedigrees from Genome-wide Estimates of Identity by Descent," The American Journal of Human Genetics, Nov. 6, 2014, vol. 95, pp. 553-564.
Sundquist, A. et al., "Effect of genetic divergence in identifying ancestral origin using HAPAA," Genome Research, Cold Spring Harbor Laboratory Press, May 2008, vol. 18, pp. 676-682.
Tipping, M. E., "Sparse Bayesian Learning and the Relevnace Vector Machine," Microsoft Research, Journal of Machine Learning Research, Jun. 2001, pp. 211-244.
United States Office Action, U.S. Appl. No. 15/209,458, May 13, 2019, 12 pages.
Weedon, M.N. et al., "Combining Information from Common Type 2 Diabetes Risk Polymorphisms Improves Disease Prediction," PLoS Medecine, Oct. 2006, vol. 3, No. 10, 6 pages.
Yang, Q. et al., "Improving the Prediction of Complex Diseases by Testing for Multiple Disease-Susceptibility Genes," Am. J. Hum. Genet., 2003, vol. 72, pp. 636-649.
Yoon, B.J., "Hidden Markov Models and their Applications in Biological Sequence Analysis," Current Genomics, 2009, Vo. 10, pp. 402-415.

* cited by examiner

Haploid Markov Model for Window $w$
200

Label Determination Method 600

LOCAL GENETIC ETHNICITY DETERMINATION SYSTEM

CROSS REFERENCE TO RELATED APPLICATIONS

This application is a continuation of prior, co-pending U.S. application Ser. No. 15/209,458, filed on Jul. 13, 2016, which claims the benefit of U.S. Provisional Application No. 62/191,968, filed Jul. 13, 2015, both of which are incorporated by reference in their entirety.

FIELD

The disclosed embodiments relate to assigning labels to an input sample genotype. In particular, the disclosed embodiments relate to using hidden Markov models that efficiently and accurately determine labels for the input sample genotype.

BACKGROUND

Although humans are, genetically speaking, almost entirely identical, small differences in human DNA are responsible for much of the variation between individuals. For example, a sequence variation at one position in DNA between individuals is known as a single-nucleotide polymorphism (SNP). Stretches of DNA inherited together from a single parent are referred to as haplotypes (e.g., one haplotype inherited from the mother and another haplotype inherited from the father).

A subset of the SNPs in an individual's genome may be detected with SNP genotyping. Through SNP genotyping, the pair of alleles for a SNP at a given location in each haplotype may be identified. For example, an SNP may be identified as heterozygous (i.e., one allele of each type), homozygous (i.e., both alleles of a same type), or unknown. SNP genotyping identifies the pair of alleles for a given genotype, but does not identify which allele corresponds to which haplotype, i.e., SNP genotyping does not identify the homomorphic chromosome (of the homomorphic pair) to which each allele corresponds. Thus, successful SNP genotyping produces an unordered pair of alleles, where each allele corresponds to one of two haplotypes.

In general, most of the SNPs of a haplotype that correspond to a particular chromosome are sourced from a single chromosome from a parent. However, some of the SNPs from the haplotype may correspond to the parent's other homomorphic chromosome due to chromosomal crossover. Because the genetic information in a particular chromosome of an individual mostly corresponds to a single chromosome of a parent, sequences of SNPs tend to stay relatively intact across generations.

SUMMARY

The computer-implemented system and method described herein assign to an input sample genotype one or more labels from a set of labels by comparing sequences of SNPs of the input sample genome those of reference sample genomes that correspond to the labels. Labels may be, for example, ethnicity labels indicating an ancestral origin group. Labels are assigned to the input sample genotype by building two types of hidden Markov models (HMMs): diploid HMMs and an inter-window HMM. Each diploid HMM is based on the SNPs in a window of one of the chromosomes of the input sample genotype. The diploid HMMs may be used to build an inter-window HMM that includes a set of states corresponding to each window across the chromosomes of the input sample genotype.

The diploid HMM is built by accessing the input sample genotype from a memory and dividing it into a number of windows, where each window includes a sequence of SNPs from the input sample genotype. A diploid HMM is built for each window based on the sequence of SNPs in that window. Each diploid state in a diploid HMM for a window may correspond to a pair of haploid states for the window, where each haploid state is from a haploid Markov model (MM). The haploid MM is a probabilistic model of a haplotype for the window. For each diploid state in a diploid HMM of a window, a diploid state probability indicating the likelihood that the input sample genotype corresponds to the diploid state is calculated.

For each window, a label pair probability distribution may be calculated based on the annotations for the window and the diploid state probabilities of the input sample genome for the diploid HMM of the window. The label pair probability distribution for a window may map each pair of labels (one label for each of two constituent haplotypes for a window) to the probability that the SNPs in the window correspond to the pair of labels. A set of annotations may be accessed, each annotation corresponding to a haploid state from a window and a label from the set of labels, where the labels include the origin groups under consideration. An annotation for a haploid state indicates the probability that a haplotype of the label (e.g., a haplotype for an individual in the origin group correspond to the label) corresponds to that haploid state. Each annotation for a label may be calculated from a set of reference samples that correspond to the labels.

An inter-window HMM may be built based on the label pair probability distributions. The inter-window HMM may include a set of states for each window, where each state in a window corresponds to a pair of labels. The transition probabilities of the inter-window HMM may be learned based on the expectation-maximization. The inter-window HMM may use the label pair probability distribution for a window as the probability distribution for each state in the window given the SNPs of the input sample genotype in the window. Based on the inter-window HMM, one or more labels may be assigned to the input sample genotype. Assigning labels may include determining a proportion of the input sample genotype that corresponds to each label, may include calculation of a Viterbi path for the inter-window HMM, and may additionally or alternatively include calculating a plurality of stochastic paths for the inter-window HMM. In some embodiments, the inter-window HMM for an input sample genotype may be used to update the annotations for use in assigning labels to other genotypes.

Compared to existing methods for assigning labels to potentially admixed genotypes, the disclosed system and methods assigns labels to a genotype quickly and accurately. The disclosed method may also update the models and/or annotations based on the genotypes which labels have been assigned to, so that the accuracy of the system improves over time.

BRIEF DESCRIPTION OF THE DRAWINGS

These and other features, aspects, and advantages of the present invention will become better understood with regard to the following description, and accompanying drawings, where.

Figure 1:
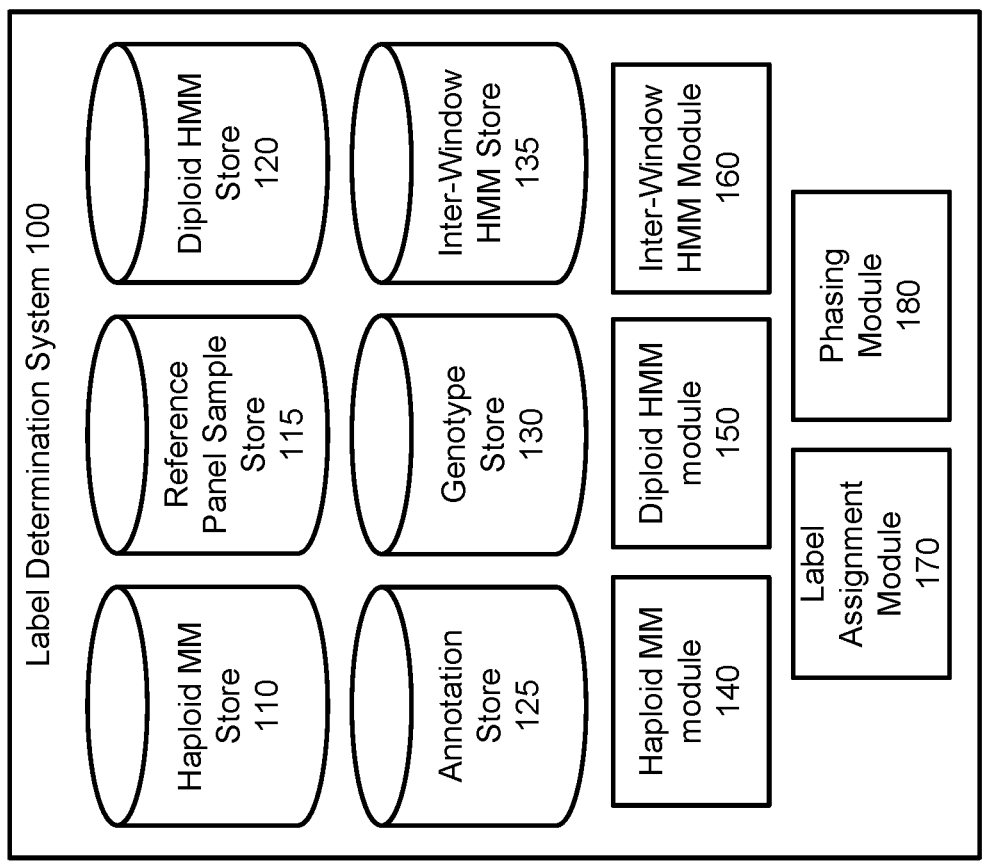
FIG. 1 is a block diagram of a label determination system for training and utilizing a model for assigning labels to a genotype, according to one embodiment.

Note that for purposes of clarity, only one of each item corresponding to a reference numeral is included in most figures, but when implemented multiple instances of any or all of the depicted modules may be employed, as will be appreciated by those of skill in the art.

DETAILED DESCRIPTION

Genetic Data Collection

Individuals may provide deoxyribonucleic acid (DNA) samples (e.g., saliva, skin cells, blood, or other biological matter) for analysis of their genetic data. In one embodiment, an individual uses a sample collection kit to provide a sample from which genetic data can be reliably extracted according to conventional methods. A DNA extraction service can receive the sample and genotype the genetic data, for example by extracting the DNA from the sample and identifying values of SNPs present within the DNA. The result is a diploid genotype. A DNA quality control and matching preparation service may assesses data quality of the diploid genotype by checking various attributes such as genotyping call rate, genotyping heterozygosity rate, and agreement between genetic and self-reported gender. The genotype data (referred to herein as a genotype) is sent (e.g., transmitted through a network) to a label determination system 100. The label determination may receive the genotype from the DNA extraction service or from the DNA quality control and matching preparation service and may store the genotype (e.g., in a database).

Genotypes may be received that includes L SNPs. Since most SNPs manifest as one of two possible allelic variations within a population (e.g., an SNP may be adenine (A) in some individuals, but cytosine (C) in others), an allele for a particular SNP of a genotype may be referenced by either 0 or 1 (e.g., 0 for A and 1 for C) without loss of generality. Furthermore, although described herein are as using biallelic SNPs (i.e., SNPs that can take on two possible alleles), the methods and systems described herein may be generalized to include multiallelic SNPs (e.g., triallelic SNPs). Additionally, instead of using individual alleles as the basic unit of genomic data, the methods and systems herein may use "mini haplotypes" consisting of multiple alleles as the basic units of data.

A pair of alleles for an SNP in a genotype may be received without information indicating the homomorphic chromosome to which each allele corresponds. Thus, genotyping may result in a sequence of L SNPs, each of which contains a unordered pair of values: (0,0) (i.e., homozygous 0), (0,1) (i.e., heterozygous), or (1,1) (i.e., homozygous 1). In some instances, genotyping a particular SNP fails, in which case the alleles for that SNP may be missing. Herein, a genotype may be represented as $G=(G_1, G_2, \ldots, G_L)$, where each $G_i$ (for $i \in \{1, \ldots, L\}$) is an SNP that has a value of either (0,0), (0,1), (1,1), or missing data. The label determination system may store and use genotypes such as a input sample genotype X that labels are assigned to and reference panel sample genomes for a label that are used to calculate an annotation for that label.

A genotype G may be divided in W windows, where each window w (for $w \in \{1, \ldots, W\}$) is a sequence of SNPs (i.e., a subsequence of G). The windows may overlap (i.e., share one or more SNPs). The bounds of each window are such that no window w includes SNPs from more than one chromosome (i.e., from more than one pair of homomorphic chromosomes). Each window w may start at SNP index $S_w$ and have a length of $D_w$. Thus, the sequence of SNPs of the genotype G in window w is $(G_{S_w}, \ldots, G_{(S_w+D_w-1)})$. The length $D_w$ of each window w may be selected so that each haplotype in the window w is likely to correspond to a single respective correct label. For example, the length $D_w$ of each window w may be selected so as to have a length of 1-10 centimorgans (cM) or less.

A input sample genome X can be assigned one or more labels by a label determination system. Each window w of the genotype G may be assigned a pair of labels from a set of K labels, one label for each haplotype in the genome G. A label is an identification of some group of haplotypes that are genetically similar. For example, a label corresponds to ancestry from a historical population (e.g., ethnic group). For example, each ethnic group and corresponding label may correspond to a geographic area which the given population historically inhabited. Examples include areas such as North Africa, Scandinavia, South Asia, etc.

System Overview

FIG. 1 is a block diagram of a label determination system for training and utilizing a model to assign labels to a genotype, according to one embodiment. The label determination system 100 trains and uses models to probabilistically determine the labels to which an input genotype sample corresponds. The label determination system 100 may be a computing system including one or more processors, one or more computer memories, and an interface for communicating through a network. In one example embodiment, the label determination system 100 includes a haploid MM store 110, a reference panel sample store 115, a diploid HMM store 120, an annotation store 125, a genotype store 130, an inter-window HMM store 135, a haploid MM module 140, a diploid HMM module 150, an inter-window HMM module 160, a label assignment module 170, and phasing module 180.

In some embodiments, the label determination system 100 may operate in a training stage and a label assignment stage. The training stage may be performed once to build haploid MMs for each window w stored in the haploid MM store 110 and calculate the annotations stored in the annotation store 125 for each label k and window w. The training stage is not based on a particular input sample genotype. After the training stage, the label determination system 100 may assign labels to an input sample genotype X during the label assignment stage. Assigning labels to an input sample genotype X uses the haploid MMs and the annotations initialized during the training phrase. After the training stage has been performed once, labels may be continuously assigned to different input sample genotypes.

Haploid Markov Model

The haploid MM store 110 stores a haploid MM for each window w. The haploid MM module 140 builds the haploid MMs based on training data (e.g., sequenced haplotypes and/or phased haplotypes) during the training stage. The haploid MMs In alternate embodiments, the haploid MMs may be received from another system (e.g., through a network). Each haploid MM is a probabilistic model of alleles in a respective window w. The haploid MM for a window w is a directed acyclic graph with a finite number of haploid states. Each directed edge between two haploid states in the haploid MM is referred to herein as a "transition" and corresponds to the value of an allele in a haplotype. Therefore, every possible haplotype (i.e., sequence of alleles) in the window w corresponds to a path (i.e., sequence of haploid states) through the haploid MM corresponding to window w. The states in a haploid MM, the transitions between them, and the probabilities of those transitions are determined by the haploid MM module 140 based on the training data. In some embodiments, a haploid MM may be a model used with a HMM phasing algorithm.

Figure 2:
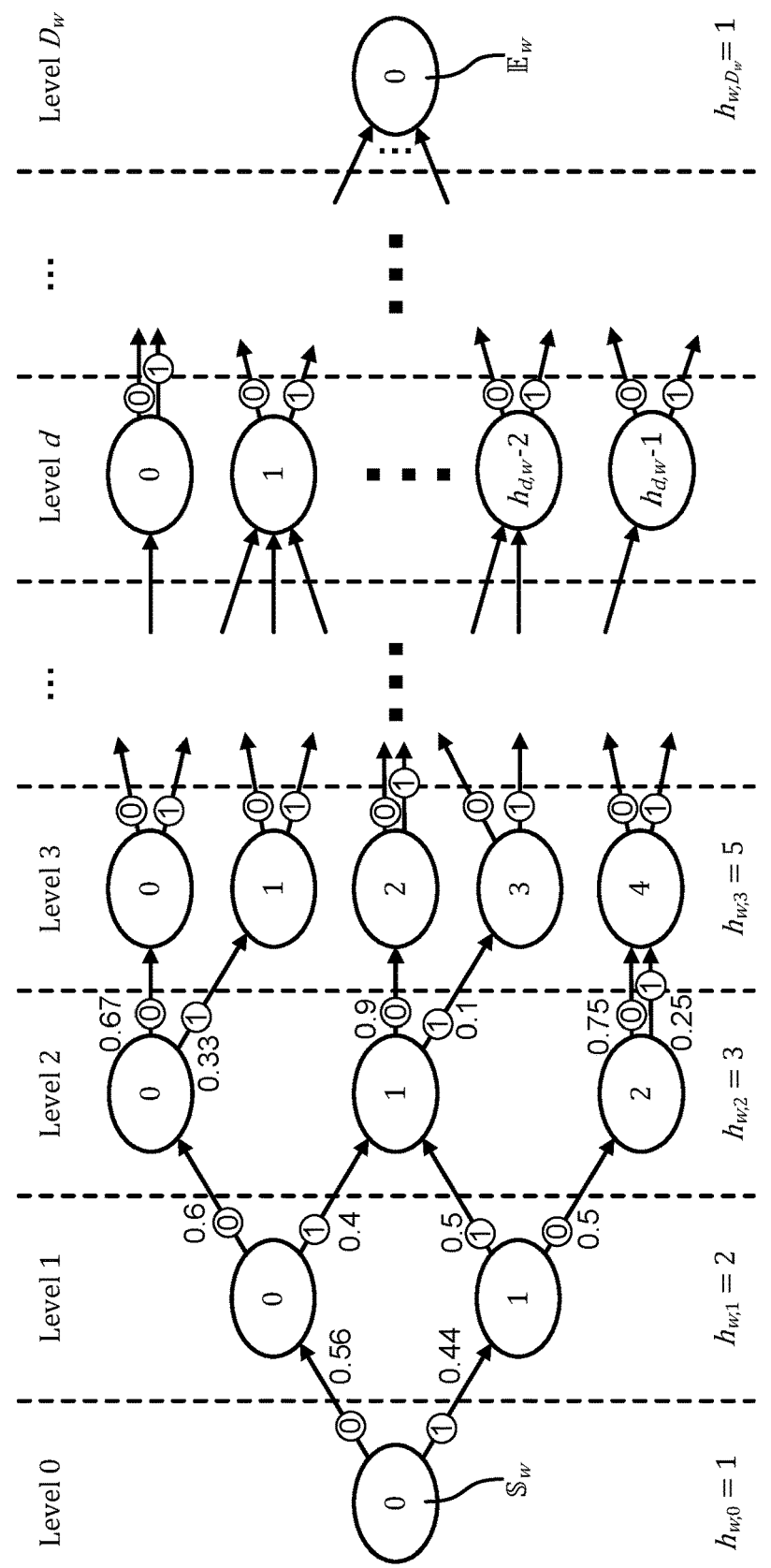
FIG. 2 is an example of a haplotype MM, according to an embodiment.

FIG. 2 illustrates an example of a haploid MM 200 for a window w, according to one embodiment. FIG. 2 illustrates the haploid MM for window w as a directed graph, where arrows represent transitions between states. The haploid MM is divided into $D_w+1$ levels (i.e., the haploid MM includes one more level than the number $D_w$ of SNPs in the window w). That is, each state in the model corresponds to some level $d \in \{0, \ldots, D_w+1\}$. Each level d in the window w includes $h_{w,d}$ states. Each state u in the haploid MM may be referenced by the combination of its level d and an index n (for $n \in \{0, \ldots, h_{w,d}-1\}$), although states may be references with an alternate referencing scheme. In FIG. 2, the index n of each state u is the integer with which the state is labeled. Herein, u(w,d,n) references the nth state at level d in window w. Thus, the start state is $\mathbb{S}_w = u(w,0,0)$ and the end state is $\mathbb{E}_w = u(w,D_w,0)$.

A haploid MM 200 includes one start state $\mathbb{S}_w$ at level 0 and one end state $\mathbb{E}_w$ at level $D_w$. Besides the end state $\mathbb{E}_w$ at level $D_w$ which is a terminal node, each state at level d can include outgoing transitions to either one or two states at level d+1. The transition between a state at level d−1 to a second state in level d corresponds to the dth allele in window w of a haplotype. In FIG. 2, the allele value of a haplotype corresponding to the transition between two states is illustrated by the number (either 0 or 1) on the arrow between the states. For example, the transition from the start state $\mathbb{S}_w$ to u(w,1,0) (i.e., the state at level 1 with index number n=0) corresponds to an allele of 0 at the first SNP position in window w and the transition from the start state $\mathbb{S}_w$ to u(w,1,1) (i.e., the state at level 1 with index number n=1) may correspond to an allele of 1 at that SNP position. As indicated by FIG. 2, in this example, the transition probability between the start state $\mathbb{S}_w$ and u(w,1,0) is 0.56 and the transition probability between $\mathbb{S}_w$ and u(w,1,1) is 1−0.56=0.44.

The transition function t(u,a) maps the haploid state u in the haploid MM for window w at level d−1 to the haploid state at level d that u transitions to when the dth allele in window w is equal to $a \in \{0,1\}$. Thus, in the example of FIG. 2, t(u(w,2,0),0) may map to haploid state u(w,3,0) and t(u(w,2,0),1) may map to haploid state u(w,3,1). When a haploid state u at level d−1 transitions to two distinct states (i.e., when t(u,0)≠t(u,1)), each of the transitions is mapped to the dth allele in the window w. Herein, p(u,a) refers to the probability that a haplotype which is in state u at level d−1 in window w has an allele with a value of a at the dth SNP in the window w. Thus, ρ(u(w,2,1),0)=0.9 and ρ(u(w,2,1),1)=0.1. If the state u transitions to only one state v at level d, then the haploid MM may still include a probability distribution for the dth allele even though the state transition is deterministic. For example, as illustrated in FIG. 2, the transition from state u(w,2,2) to state u(w,3,4) may associate a probability of 0.75 with allele 0 at the third SNP in the window w and a probability of 0.25 for allele 1 at the third SNP in the window w.

Each path through the haploid MM 200 corresponds to one or more possible sequences of alleles (for example, that may occur in the input sample genotype X). The probability of a sequence of alleles is given by the product of the corresponding allele probabilities in the corresponding path. For example, a path that includes the sequence of state ($\mathbb{S}_w$, u(w,1,1), u(w,2,1), u(w,3,3)) corresponds to the sequence of alleles (1,1,1) which has a probability of $\rho(\mathbb{S}_w,1) \times \rho(u(w,1,1),1) \times \rho(u(w,2,1),1) = 0.022$. The possible haplotypes (or, equivalently, every possible sequence of alleles) correspond to different paths in the haploid MM. Each path corresponding to a possible haplotype begins at the start state $\mathbb{S}_w$, includes exactly one state for each level d, and ends at the end state $\mathbb{E}_w$.

Diploid Hidden Markov Model

Returning to FIG. 1, the diploid HMM store 120 stores a diploid HMM for each window w. The diploid HMM module 150 may build these diploid HMMs based on the haploid MMs stored in the haploid MM store 110. Each diploid state in the diploid HMM for window w corresponds to an ordered pair of haploid states (i.e., one haploid state for each of the two haplotype that constitute a genome) in the haploid MM 200 for window w. Thus each diploid state $(u_1, u_2)$ in the diploid HMM at level d corresponds to the haploid states $u_1$ and $u_2$, where $u_1$ and $u_2$ are from level d. For example, the start state of the diploid HMM for window w is (u(w,0,0), u(w,0,0))=($\mathbb{S}_w, \mathbb{S}_w$).

In some embodiments, the diploid HMM store 120 stores a full HMM for each window w. A full diploid HMM for window w includes, for a level d, a diploid state for every ordered pair of haploid states in the haploid MM 200 at level d. Full diploid HMMs may be calculated during the training stage. The diploid HMM store may also include diploid HMMs that correspond to particular genotypes. The diploid HMM for a particular genotype G (e.g., an input sample genotype X or a reference panel sample genome for a label k) in window w may include all the possible diploid states that are compatible with the genotype G and the possible transitions for genotype G. Diploid HMMs may be built for the input sample genome X by the diploid HMM module 150 during the label assignment stage. Diploid HMMs may be also be built by the diploid HMM module for the reference panel sample genomes stored in the reference panel sample store 115 during the training stage when calculating the annotations in the annotation store 125. In general, the diploid HMM for window w for a genotype G includes fewer states than the full diploid HMM for window w, because many diploid states in the full diploid HMM will not be compatible with the genotype G.

In some embodiments, the diploid HMM for a genotype G for a window w is built based on the full diploid HMM for the window w. In alternate embodiments, the diploid HMM module 150 does not build full diploid HMMs and no full diploid HMMs are stored in the diploid HMM store 120. Instead, the diploid HMM module may build diploid HMMs for genotypes for each window w based on the corresponding haploid MM for window w.

Figure 3:
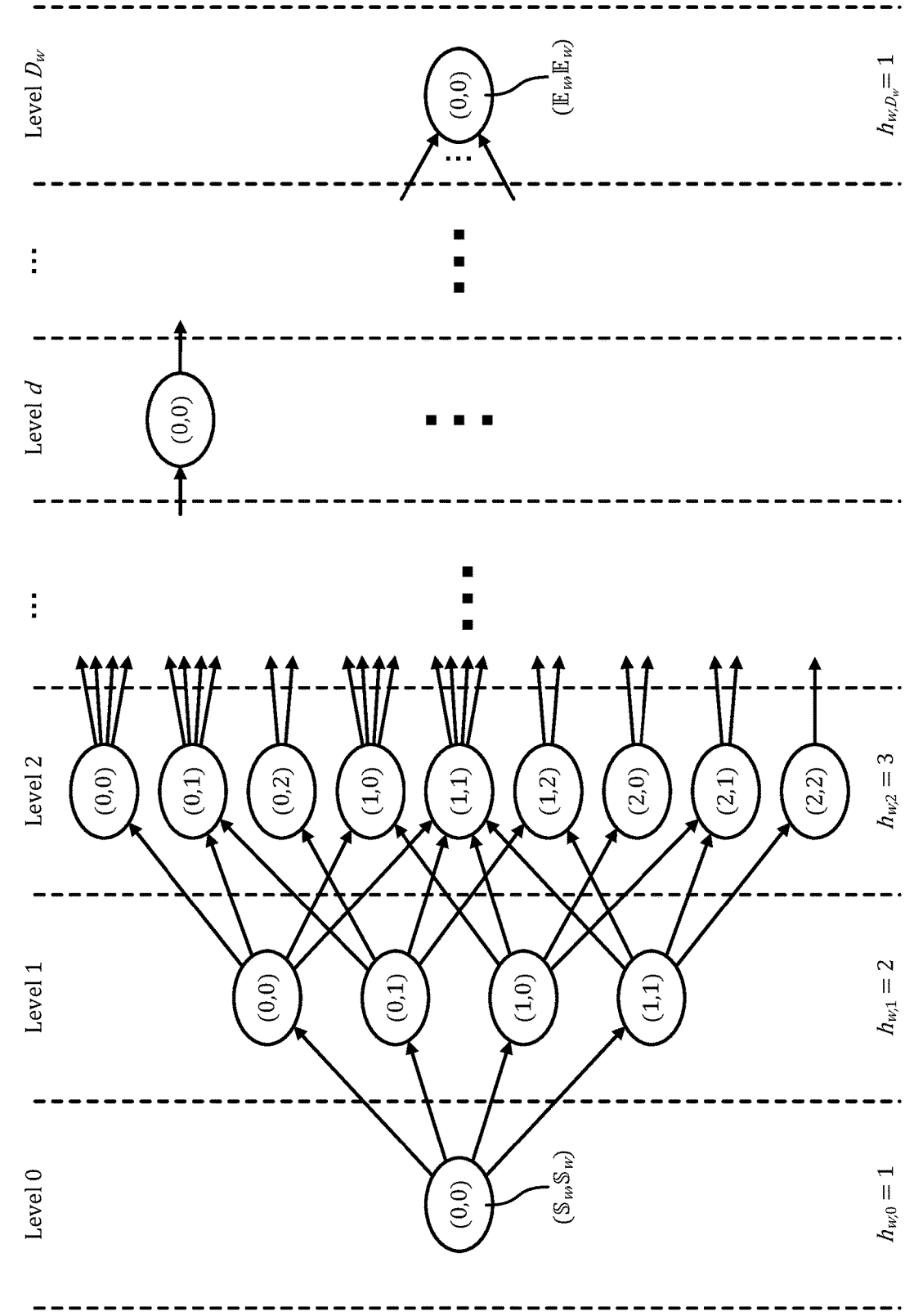
FIG. 3 is an example of a diploid HMM, according to an embodiment.

FIG. 3 is an example of a diploid HMM 300 for a window w, according to an embodiment. The diploid HMM illustrated in FIG. 3 is a fully-instantiated diploid HMM. For this reason, the number of diploid states at each level d for window w is equal to the square of the number of states in the corresponding haploid MM 200 at level d (i.e., $(h_{w,d})^2$). For a genotype sequence made up of haplotypes that correspond to a diploid state $(u_1,u_2)$ at level d−1 in a window w, the probability that the dth genotype in the window w is the ordered pair $(a_1,a_2)$ equals $\rho(u_1,a_1)\times\rho(u_2,a_2)$. The number of possible transitions from a diploid state $(u_1,u_2)$ is equal to the number of possible transitions from $u_1$ in the haploid MM multiplied by the number of possible transitions from $u_2$.

FIG. 3 depicts an example diploid HMM 300 that corresponds to the example haploid MM 200 depicted in FIG. 2. In FIG. 2, each diploid state in the diploid HMM is labeled with a pair of index numbers (n,m) corresponding to the indices of the corresponding pair of haploid states in the haploid MM. For example, the diploid state labeled (1,2) at level 2 in FIG. 3 represents the diploid state (u(w,2,1),u(w, 2,2)) where haploid states u(w,2,1) and u(w,2,2) are from the haploid MM 200 of FIG. 2.

Because every genotype corresponds to two haplotypes, each phased genotype corresponds to a single path through the diploid HMM 300 for window w. However, because the SNPs in unphased genotypes do not associate alleles with particular haplotypes, the exact path through the diploid HMM that a genotype traverses will likely be ambiguous as the genotype will likely include a number of heterozygous SNPs and possibly missing data for SNPs as well. For example, the sequence of unordered allele pairs ((0,1),(0,1)) corresponds to four distinct paths through the first three levels of the example diploid HMM for window w such as the sequence of diploid states (($\mathbb{S}_w$, $\mathbb{S}_w$),(u(w,1,0),u(w,1, 1)),(u(w,2,1),u(w,2,2))).

Various modifications may be made to the diploid HMM 300 as described above. For example, because the probability of transition from diploid state $(u_1,u_2)$ to diploid state $(u_3,u_4)$ is equivalent to the probability of the transition from $(u_2,u_1)$ to $(u_4,u_3)$, diploid states in an diploid HMM may be collapsed/reduced into states representing unordered pairs. This reduces both the computer processing time required and the complexity of the calculation.

The diploid HMM module 150 calculates a label pair probability distribution $E_{X,w}$ for each window w for a input sample genotype X. The label pair probability distribution $E_{X,w}$ includes a label pair probability $E_{X,w}(p,q)$ for each unordered pair of labels (p,q). The label pair probability distribution $E_{X,w}(p,q)$ is a metric indicating the agreement between the input sample genome X and the annotations for the label pair (p,q). For each window w of a input sample genotype X and each pair of labels (p,q), the calculated label pair probability $E_{X,w}(p,q)$ is equal to or proportional to the probability of the input sample genotype X in the window w given that the haplotypes of the genome in window w correspond to the pair of labels (p,q). In some embodiments, the label pair probability distribution $E_{X,w}(p,q)$ is normalized so that the summation of the distribution is the same for each window (e.g., $E_{X,w}(p,q)$ may be a normalized probability such that $\sum_{p=1}^{K}\sum_{q=p}^{K} E_{X,w}(p,q)=1$). In some embodiments, the label pair probability distribution $E_{X,w}$ is based on the SNPs in window w of the genotype X but not on SNPs of the genotype X outside of window w. The label pair probability distribution $E_{X,w}$ may be based on an diploid HMM for the window w and the input sample genotype X.

Annotations

Returning now to FIG. 1, the reference panel sample store 115 stores a set of reference samples for each of the K labels. The set of reference panel samples corresponding to the kth label (for k∈{1, . . . , K}) is referred to herein as $R_k$. Each reference panel sample R∈$R_k$ in the store 115 may be an unphased diploid genotype of L SNPs, R=($R_1$, . . . , $R_L$), where each $R_i$ (for i∈{1, . . . , L}) is an SNP that is either an unordered pair of binary alleles (i.e., (0,0), (0,1), or (1,1)) or missing data. The labels may each correspond to a different origin population (e.g., an ethnic group), in which case each reference panel sample R may be a single-origin genotype from the kth origin population.

The annotation store 125 stores an annotation $A_w(k,u)$ for each label k and for each haploid state u in the haploid MM 200 for window w. The annotations may be calculated by the diploid HMM module 150 during the training stage. An annotation is $A_w(k,u)$ is based on the set of reference panel samples $R_k$ for the label k. The annotation $A_w(k,u)$ is based on a calculation, for each reference sample R∈$R_k$, of the conditional probability of the haploid state u given the SNP sequence in the window w for the reference panel sample R. The calculation of the probability of the state u given reference panel sample R is based on the haploid MM 200 for window w. For a given window w, label k, and state u, the annotation $A_w(k,u)$ is the probability that a haplotype corresponding to label k includes the haploid state u in its path through window w. Equivalently, the annotation $A_w(k, u)$ is the expected proportion of haplotypes of the genotypes of the set of reference panel samples $R_k$ that include haploid state u in their corresponding paths.

In one embodiment, annotations are determined using a forward-backward algorithm. For a reference panel sample R∈$R_k$, the forward-backward algorithm may be used to calculate a forward function $f_{R,w}$ and a backward function $b_{R,w}$. The forward function $f_{R,w}(u,v)$ may map the diploid state (u,v) at level d to the joint probability of the first d SNPs in window w of the reference panel sample R and the diploid state (u,v). That is, the output of the forward function $f_{R,w}(u,v)$ is the probability, based on the haploid MM for the window w, that a genotype has the first d SNPs of R and that R corresponds to the state (u,v) at level d. Similarly, the backward function $b_{R,w}(u,v)$ may map the diploid state (u,v) at level d to the joint probability of the last (D-d) SNPs in window w of the reference panel sample R and the state (u,v). The forward-backwards product, $f_{R,w}(u,v)\times b_{R,w}(u,v)$, may be the joint probability of all the SNPs of the reference panel sample R in window w and the corresponding state (u,v). In some embodiments, the outputs of the forward function $f_{R,w}$ and the backward function $b_{R,w}$ are proportional, but not necessarily equal to the probabilities of their respective diploid states.

The annotation $A_w(k,u)$ for the label k and state u may be given by:

$$A_w(k, u) = \frac{1}{|R_k|} \sum_{R \in R_k} \frac{1}{b_{R,w}(\mathbb{S}_w, \mathbb{S}_w)} \sum_{v \in StatesInLevel_w(u)} f_{R,w}(u, v) \times b_{R,w}(u, v) \quad (1)$$

where $|R_k|$ denotes the cardinality of the set $R_k$ (i.e., the number of reference panel samples in $R_k$) and where $StatesInLevel_w(u)$ refers to the set of haploid states in the same level as u (i.e., if u is in level d, then $StatesInLevel_w(u)$ is the set of all states at level d). Because ($\mathbb{S}_w$, $\mathbb{S}_w$) is the start state of the diploid HMM 300 for window w, $b_{R,w}$($\mathbb{S}_w,\mathbb{S}_w$) is equal to the likelihood of the reference panel sample R.

By the definition of the conditional probability, $f_{R,w}(u,v)\times b_{R,w}(u,v)/b_{R,w}(\mathbb{S}_w,\mathbb{S}_w)$ is the diploid state probability, i.e., the conditional probability that the path of a genotype includes the state (u,v) in the diploid HMM 300 for window w given that the genotype is the reference panel sample R.

In some embodiments, the forward-backwards product $f_{R,w}(u,v) \times b_{R,w}(u,v)$ and $b_{R,w}(\mathbb{S}_w, \mathbb{S}_w)$ are calculated to be proportional, but not necessarily equivalent, to the likelihood of their respective diploid states. In such an embodiment, the diploid state probability $f_{R,w}(u,v) \times b_{R,w}(u,v)/b_{R,w}(\mathbb{S}_w, \mathbb{S}_w)$ for reference panel sample R is still equivalent to the conditional probability that the path of the genotype includes the state (u,v) in the diploid HMM 300 given the genotype R.

The summation of the diploid state probabilities $f_{R,w}(u,v) \times b_{R,w}(u,v)/b_{R,w}(\mathbb{S}_w, \mathbb{S}_w)$ over all haploid states v in level d produces the marginal probability that the first haplotype is in haploid state u at level d given the reference panel sample R. The diploid state probabilities for a reference panel sample R may be summed over the set of diploid states that include the haploid state u (i.e., diploid states (u,v) and (v,u) for all haploid states v at the same level as the haploid state u) to produce a probability that the reference panel sample R corresponds to the haploid state u. Finally, the probabilities of u for each reference panel sample R may be combined produce the annotation $A_w(k,u)$. For example, $A_w(k,u)$ may be the arithmetic average of the probabilities of the haploid state u for each reference panel sample R, therefore representing the expected proportion of reference panel samples in the set of reference panel samples $R_k$ that include the state u in their respective paths. Stated differently, the annotation $A_w(k,u)$ is the probability that the haploid state of a haplotype at a level d is haploid state u given that the haplotype corresponds to label k. In other alternatives, a different mathematical formulation other than arithmetic average may be used.

The annotations in the annotation store 125 may be calculated during a training stage prior to determining labels for potentially admixed genotypes. In some embodiments, the annotations are updated based on labels determined for unphased potentially admixed genotypes that are input to the system through the process described herein. In some embodiments, the annotations $A_w(k,u)$ for a label k and window w may be iteratively improved by determining a probability that an admixed genotype corresponds to a label k in window w and modifying the annotations $A_w(k,u)$ accordingly.

Inter Window Hidden Markov Model

After the training stage is complete, the label determination system 100 begins the label assignment phase to assign labels to an input sample genome X. The genotype store 130 stores one or more unphased genotypes, including the input sample genotype X. The label determination system 100 may assign one or more labels to the input sample genotype X based on the sequence of SNPs in the input sample genotype X. The inter-window HMM store 135 stores an inter-window HMM corresponding to the input sample genotype X that is used to determine the labels. The inter-window HMM is built by the inter-window HMM module 160. The inter-window HMM includes states for each window w. The transition probabilities between states in the inter-window HMM may be based on the annotations or some subset thereof as stored in the annotation store 125.

Figure 4:
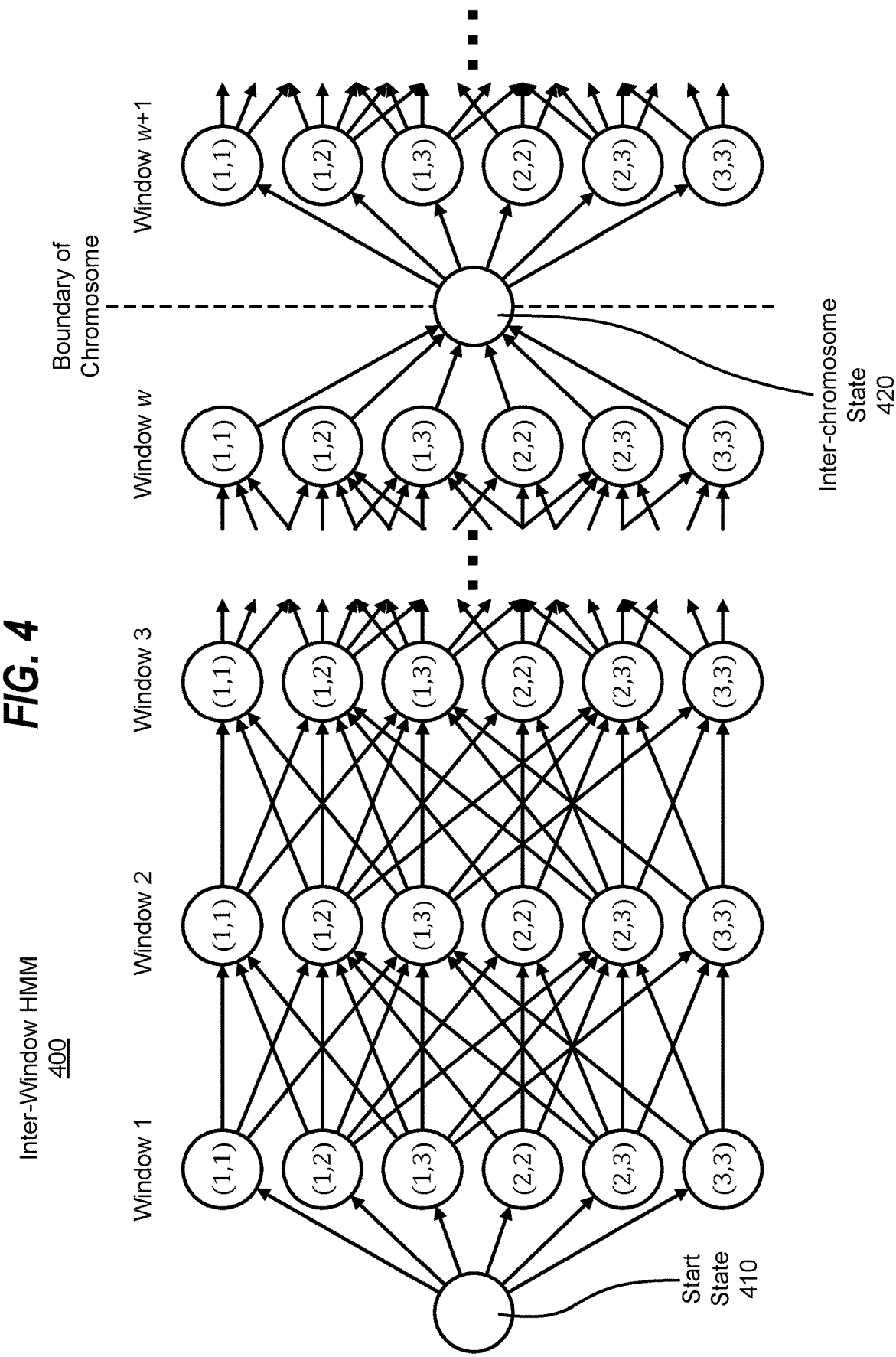
FIG. 4 is an example of an inter-window HMM, according to an embodiment.

FIG. 4 is a simplified example of an inter-window HMM 400 such as may be stored in the inter-window HMM store 135, according to an embodiment. For each window w, an inter-window HMM includes a set of states corresponding to every unordered pair of labels from the set of labels K. Thus, there are T=(K+1)K/2 states for each window w. Herein, the states for a window w are denoted as $U_{X,w,(p,q)}$ where (p,q) corresponds to a pair of labels. For the purpose of clarity, the values of p and q are restricted to $1 \leq p \leq q \leq K$. In this way, the pair (p,q) uniquely refers to each of the T unordered pairs of labels.

For purposes of illustration, FIG. 4 shows an example of an inter-window HMM 400 with K=3 labels. Thus, in the embodiment illustrated by FIG. 4, each window w has T=6 states, each state corresponding to a pair of labels $(p,q) \in \{(1,1),(1,2),(1,3),(2,2),(2,3),(3,3)\}$. Although FIG. 4 depicts K=3 labels, the number of labels K can selected to be any natural number. The start state 310 transitions to one of the T possible states of window 1 as illustrated by the six arrows between the start state 310 and the respective T states of window 1. Each state in window 1 transitions to states in window 2. A state $U_{X,w,(p,q)}$ in window w may transition to a state $U_{X,w+1,(p',q')}$ in window w+1, where $1 \leq p' \leq q' \leq K$. If the window w and the window w+1 correspond to the same chromosome (i.e., correspond to the same pair of homomorphic chromosomes), then a state $U_{X,w,(p,q)}$ may be more likely to transition to a state $U_{X,w+1,(p',q')}$ in window w+1 that corresponds to the same pair of labels (i.e., (p',q')=(p,q)) than to a state in window w+1 that corresponds to a different pair of labels (p',q'), where $1 \leq p' \leq q' \leq K$. This is because it is biologically unlikely that the sequences of SNPs in adjacent windows will correspond to different labels (e.g., correspond to different ancestral origin groups). In some embodiments, the inter-window HMM may include a probability that sequential states from the same chromosomes correspond to the same pair of labels. Herein, this probability is denoted as $(1-\tau_X)$.

In some embodiments, the transition probability $P_X(U_{X,w,(p,q)},(p',q'))$ from a state $U_{X,w,(p,q)}$ to a state $U_{X,w+1,(p',q')}$ in the same chromosome is given by:

$$P_X(U_{X,w,p,q},(p',q')) = \begin{cases} 0, & \text{if } p' \notin \{0,q\} \text{ and } q' \notin \{p,q\} \\ 1-\tau_X, & \text{if } p=p' \text{ and } q=q' \\ \tau_X \times \pi_{X,(p',q')}, & \text{otherwise} \end{cases} \quad (2)$$

where $\pi_{X,(p',q')}$ is the label probability corresponding to the pair of labels (p',q') and where the label change probability $\tau_X$ is the probability that one of the labels (p',q') in state $U_{X,w+1,(p',q')}$ will have one label different than (p,q) in state $U_{X,w,(p,q)}$. A label probability vector $\pi_X$ may include the label probabilities $\pi_{X,(p,q)}$ for all $1 \leq p \leq q \leq K$. The values of $\pi_X$ and $\tau_X$ may be calculated by the inter-window HMM module 160 based on the input sample genotype X according to a procedure described below. In some embodiments, the label probabilities $\pi_{X,(p,q)}$ sum to unity (i.e., $\Sigma_{p=1}^{K} \Sigma_{q=p}^{K} \pi_{X,(p,q)} =1$). In some embodiments, the values of the label probability vector $\pi_X$ and the label change probability $\tau_X$ are calculated with a Baum-Welch algorithm. In Equation 2, transitions from a state $U_{X,w,(p,q)}$ to a state $U_{X,w+1,(p',q')}$ without any of the same labels (i.e., if $p' \notin \{p,q\}$ and $q' \notin \{p,q\}$) are impossible. By omitting a transition for these low-probability transitions, the complexity of the inter-window HMM 400 may be reduced, thereby producing significant savings in time and computer processing requirements needed to determine labels.

In some embodiments, for some states $U_{X,w,(p,q)}$, the outgoing transition probabilities do not sum to unity (i.e., $\Sigma_{p'=1}^{K} \Sigma_{q'=p'}^{K} P_X(U_{X,w,p,q},(p',q')) < 1$). Defining the transition probabilities to sum to less than unity may decrease the complexity compared to embodiments in which the transition probabilities are normalized so as to sum to unity. For example, in embodiments in which the transitions probabilities between states on the same chromosome is given by equation 2, the outgoing transition probabilities for a state on a window w that is on the same chromosome as window w+1 do not sum to unity. In such embodiments, a state $U_{X,w,(p,q)}$ may have outgoing transitions to states in window w+1 and to an implicit null state that does not have outgoing transitions. In some embodiments, the inter-window HMM 400 does not explicitly reference these null states or the transitions thereto. In some embodiments, the inter-window HMM functionally ignores these implicit null states.

If the window w+1 corresponds to a different chromosome than window w, then the state $U_{X,w,(p,q)}$ may transition to an inter-chromosome state 320, which, in turn, transitions to a state $U_{X,w+1,(p',q')}$ in the next window w+1. Thus, if the window w+1 corresponds to a different chromosome than window w, the state $U_{X,w,(p,q)}$ may transition to a state $U_{X,w+1,(p',q')}$ with a probability that is independent of the state $U_{X,w,(p,q)}$ at window w (i.e., independent of (p,q)) because of the intervening inter-chromosome state 320. The transition probability between consecutive windows w and w+1 corresponding to different chromosomes may be given by:

$$P_X(U_{X,w,p,q},(p',q')) = \pi_{X,(p',q')} \quad (3)$$

If window w is the final window (i.e., w=W), then the state $U_{X,w,(p,q)}$ in the window w transitions to an end state (not shown in FIG. 4). Each state $U_{X,w,(p,q)}$ in window w transitions to either a state $U_{X,w+1,(p,q)}$ in window w+1, an inter-chromosome state 320, or an end state. FIG. 4 illustrates the possible outgoing transitions for each state $U_{X,w,(p,q)}$ with arrows. For example, in window 2 (and in all windows w in which the window w+1 is on the same chromosome), the state $U_{X,2,(1,3)}$ corresponding to the pair of labels (1,3) has five outgoing arrows because $U_{X,2,(1,3)}$ can transition to the states $U_{X,3,(1,1)}$, $U_{X,3,(1,2)}$, $U_{X,3,(1,3)}$, $U_{X,3,(2,3)}$, and $U_{X,3,(3,2)}$. However, state $U_{X,2,(1,3)}$ cannot transition to state $U_{X,2,(2,2)}$ because this state does not share any common labels with state $U_{X,2,(1,3)}$. Similarly, state $U_{X,1,(1,1)}$ can transition to three states ($U_{X,1,(1,1)}$, $U_{X,1,(1,2)}$ and, $U_{X,1,(1,3)}$), but cannot transition to states $U_{X,1,(2,2)}$, $U_{X,1,(2,3)}$, and, $U_{X,1,(3,3)}$. In general, when w and w+1 are on the same chromosome, a state $U_{X,w,(p,q)}$ with two different labels (i.e., p≠q) can transition to 2K−1 states $U_{X,w+1,(p',q')}$ and a state $U_{X,w,(p,p)}$ with two of the same labels can transition to K states $U_{X,w+1,(p',q')}$.

In some embodiments, the inter-window HMM module 160 uses the label pair probability distribution $E_{X,w}$ as the emission probabilities for states in window w. That is, the label pair probability $E_{X,w}(p,q)$ may be an estimate of the probability of the sequence of SNPs $(X_{S_w}, \ldots, X_{(S_w+D_w-1)})$ in window w given that the state for window w is $U_{X,w,(p,q)}$). The label pair probability distribution may be normalized so that all windows in the inter-window HMM are weighted equally. In some embodiments, the inter-window module calculates a forward function $F_X$ and a backward function $B_X$ for the inter-window HMM. For a state $U_{X,w,(p,q)}$ in the inter-window HMM, the forward function $F_X(w,p,q)$ may be the probability that the input sample genotype X corresponds to the labels (p,q) in window w given the SNP sequences of the first w windows. Similarly, the backward function $B_X(w,p,q)$ may be the probability that the input sample genotype X corresponds to the label (p,q) in the window w given the SNP sequences in window w to window W. The inter-window HMM module may also calculate the vector of label probabilities $\pi_X$ and the label change probability $\tau_X$ based on the label pair probability distribution $E_{X,w}$.

Label Assignment

Returning now to FIG. 1, the label assignment module 170 determines one or more labels for the input sample genotype X based on the inter-window HMM. In some embodiments, the label assignment module 170 may determine a proportion of the input sample genotype X that corresponds to each label. For example, the label assignment module 170 may determine that 25% of the input sample genotype X corresponds to label 1, 0% corresponds to label 2, 50% corresponds to label 3, and 25% corresponds to label 4. The proportion of each label may be based on the states in the Viterbi path, based on the probability of being in each state (e.g., as calculated with the forward-backward algorithm), or otherwise based on the inter-window HMM. The determination of these proportions may also be based on a weight assigned to each window w. The weight of each window w may be based on the size of the window (e.g., in number of bases). The weighting of each window w may be adjusted based on portions of the windows w that overlaps with other windows.

In some embodiments, the label assignment module 170 assigns a pair of labels to each window w of the input sample genotype X. In some embodiments, the label assignment module 170 determines the Viterbi path through the inter-window HMM 400. In alternate embodiments, the label assignment module 170 computes a number (e.g., 1000) of stochastic paths through the inter-window HMM and determines a range of each label's proportion based on the states taken by the stochastic process. For example, the label assignment module 170 may determine that 18-30% of the input sample genotype X corresponds to a particular label. The range may be based on the maximum and minimum proportion of the genotype X that corresponds to a label in the stochastic paths. Alternately, the range may be based on percentiles of the proportions of the input sample genotype X that corresponds to a label in the stochastic paths. For example, the upper bound of a range for label k may be based on a 95th percentile of the proportions of the states that correspond to label k in the stochastic paths and the lower bound may be based on the 5th percentile.

In some embodiments, the label assignment module 170 assigns labels to specific portions of the input sample genotype X. The label assignment module 170 may specifically assign labels to a portion of the input sample genotype X that corresponds to one or more overlapping regions with a second genotype. For example, if the input sample genotype and the second genotype are the genotypes of related individuals (e.g., first cousins), then the one or more overlapping are the regions of genetic information that correspond to one or more shared ancestors (e.g., a grandmother and a grandfather shared by the cousins). If, in an overlapping region, there is only one haplotype (in each genotype) that overlaps between the input sample genotype X and the second genotype, the label assignment module 170 may assign labels specifically to the overlapping haplotype.

The phasing module 180 may probabilistically separate the input sample genotype X into its constituent haplotypes based on the assigned labels. In one embodiment, a pair of labels for each window w is assigned based on the Viterbi path through the inter-window HMM. Phasing (i.e., separating the input sample genotype X into haplotypes) may be performed based diploid HMMs 300 for each window w modified by the annotations $A_w$ for the assigned labels. For example, the diploid HMM for the input sample genotype X may be modified so that the probability of the diploid state $(u_1,u_2)$ in the window w is given by $A_w(u_1,p) \times A_w(u_2,q)$ $f_{X,w}(u_1,u_2) \times b_{X,w}(u_1,u_2)/b_{X,w}(\mathbb{S}_w,\mathbb{S}_w)$. The SNPs in the window w may be phased into the constituent haplotypes by determining the Viterbi path through the modified diploid HMM. In this way, the genome X may be phased so as to maximize the agreement with the label assignment. The haplotypes may also be combined across windows. For example, if the labels (p,q) were assigned to window w and the labels (p,q') were assigned to window w+1, then the sequence of alleles in the phased haplotype corresponding to label p in window w may be combined with the sequence of alleles in the phased haplotype corresponding to label p in window w+1. Similarly, the sequence of alleles in the phased haplotype corresponding to label q in window w may be combined with those of label q' in window w+1.

The label determination system 100 comprises one or more processors and one or more non-transitory computer readable storage mediums. The one or more processors may implement the functions attributed above to modules. The modules may be hardware modules (i.e., computer hardware specially configured to perform specific functions), software modules, or some combination thereof. The non-transitory computer readable mediums may store computer instructions that, when executed, perform the methods described herein. In some embodiments, the label determination system 100 is a single computing system. In alternate embodiments, the label determination system 100 may be a distributed system including spatially-separated databases and computing systems (e.g., servers) that communicate via a network.

Training the Label Determination System

Figure 5:
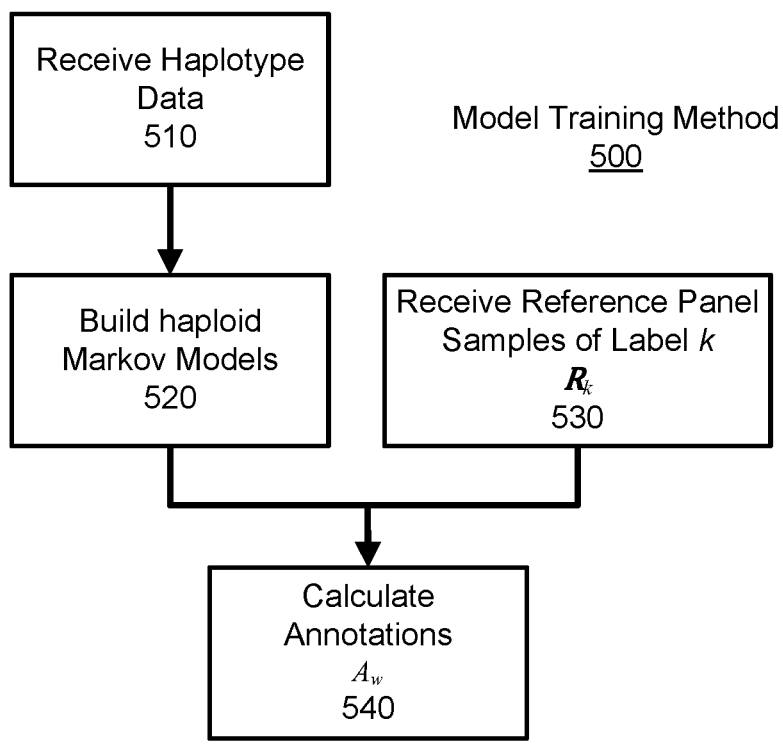
FIG. 5 is a flowchart illustrating a method for calculating annotations, according to some embodiments.

FIG. 5 is a flowchart illustrating a method for calculating annotations, according to some embodiments. The model training method may be performed by the label determination system 100 during the training stage. For each window w, the model training method produces a haploid MM 200 and a set of annotations $A_w$. The annotations $A_w(k,u)$ for label k and window w may be based on the set of reference panel samples $R_k$ and the haploid MM for window w.

In the model training method 500, haplotype data is received 510 by the label determination system 100. The haplotype data may be a sequence of alleles corresponding to individuals. Each sequence of haplotype data may include alleles corresponding to the L SNPs of the genotypes stored in the genotype store 130, or some subset thereof. Some or all of the haplotype data may be phased haplotype data produced by the method described in the PCT application entitled "Haplotype Phasing Modules" (International Publication Number WO 2016/061568 A1) which was filed on Oct. 19, 2015 and which is hereby incorporated by reference in its entirety. In alternate embodiments, some or all of the haplotype data may be phased haplotypes produced by PHASE, BEAGLE, HAPI-UR, SHAPEIT2, IMPUTE2, or some other phase estimation method. Based on the received haplotype data, the haploid MM module 140 builds 520 haploid MMs 200 for each window w. The haploid MMs may be stored in the haploid MM store 110.

The label determination system 100 also receives 530 a set of reference panel samples $R_k$ for each label k (for 1≤k≤K). The set of reference panel samples $R_k$ may be accessed from the reference panel sample store 115. Based on the set of reference panel samples $R_k$ for label k and the haploid MMs for window w, the diploid HMM module 150 may calculate a set of annotations $A_w(k,u)$ of every label k and every state u in the window w. The annotations $A_w$ may be stored in the annotation store 125.

Determining Labels for a Genotype

Figure 6:
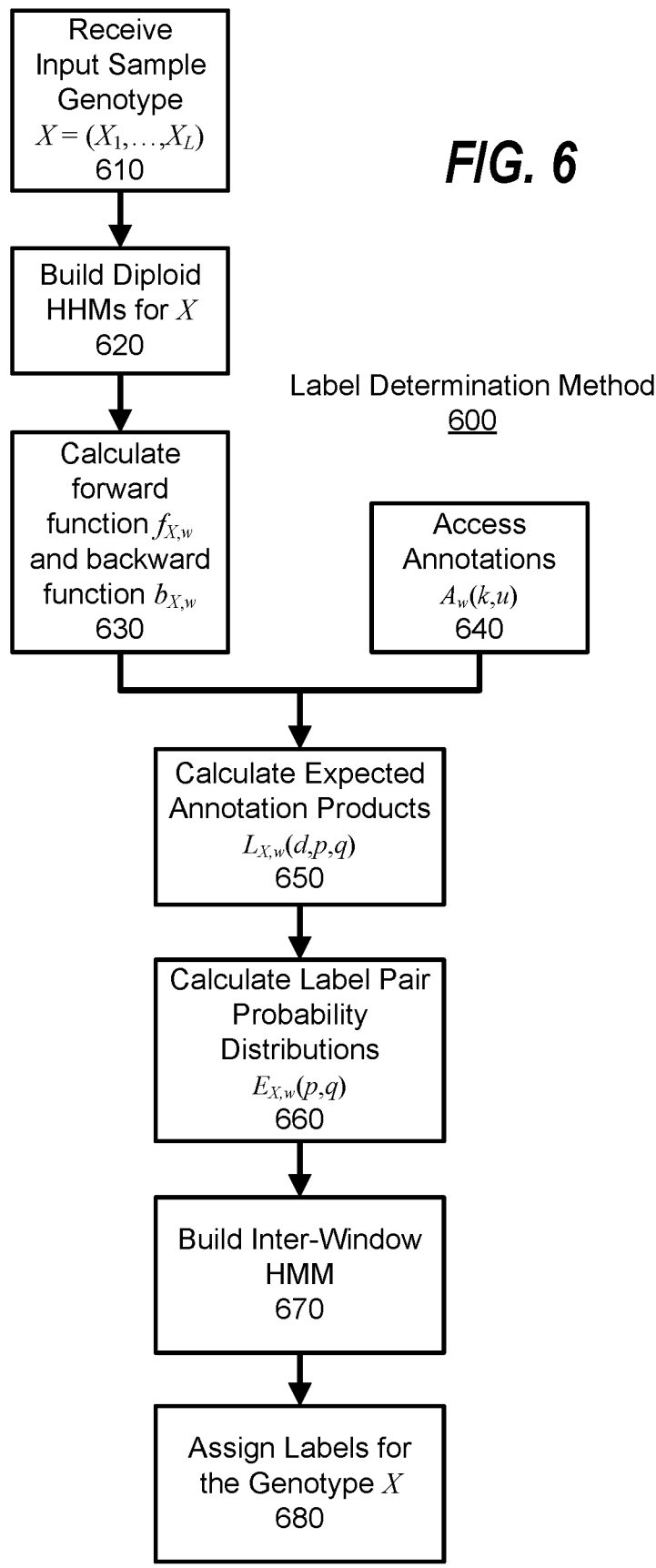
FIG. 6 is a flowchart illustrating a method for assigning labels to a genotype, according to some embodiments.

FIG. 6 is a flowchart illustrating a method for assigning labels to a genotype, according to some embodiments. The label determination method 600 may be performed by the label determination system 100.

The label determination system 100 receives 610 an input sample genotype X. Based on the input sample genotype X, the diploid HMM module 150 builds 620 a diploid HMM 300 for X each window w. When building 620 the diploid HMMs, the diploid HMM module 150 may determine $\alpha_{X,w}(d)$, the set of possible diploid states (u,v) at level d that the genotype X can traverse. The diploid HMM module 150 may also calculate 630 the forward function $f_{X,w}$ and the backward function $b_{X,w}$ for the diploid HMM of each window w so as to determine the probability that the genotype X corresponds to each diploid state (u,v) with a forward-backward algorithm. In some embodiments, the set of possible diploid states $\alpha_{X,w}(d)$ is determined with the forward-backward algorithm as discussed above.

Based on the annotations $A_w(k,u)$ and the input sample genotype X, the diploid HMM module 150 may calculate 650 an expected annotation product $L_{X,w}(d,p,q)$ for level d and for an unordered pair of labels (p,q). The expected annotation product $L_{X,w}(d,p,q)$ may be the probability that a stochastic genotype with haplotypes of respective labels p and q corresponds to the same diploid state at level d as the input sample genotype X given the genotype sequence (i.e., given $(X_{S_w}, \ldots, X_{(S_w+D_w-1)})$) in window w. The expected annotation product $L_{X,w}(d,p,q)$ may be based on the annotations for the $A_w(p,u)$ $A_w(p,v)$, $A_w(q,u)$, and $A_w(q,v)$ for the diploid state (u,v) at level d. The expected annotation product $L_{X,w}(d,p,q)$ may be given by:

$$L_{X,w}(d, p, q) = \sum_{(u,v) \in \alpha_{X,w}(d)} \frac{f_{X,w}(u, v) b_{X,w}(u, v)}{2 \times b_{X,w}(\text{start}_w, \text{start}_w)} (A_w(p, u) A_q(q, v) + A_w(q, u) A_w(p, v)) \quad (4)$$

where $\alpha_{X,w}(d)$ is the set of possible diploid states (u,v) at level d that the input sample genotype X can include. In some embodiments, the set of possible diploid states $\alpha_{X,w}(d)$ is determined with the forward-backward algorithm.

Each expected annotation product $L_{X,w}(d,p,q)$ may be normalized across all the different values of (p,q) and averaged together from level 1 to level D to calculate 660 a label pair probability distribution $E_{X,w}(p,q)$ for the window w. The label pair probability $E_{X,w}(p,q)$ for window w is a metric indicating the likelihood that the window w corresponds to the pair of labels (p,q) given the input sample genotype X in the window w. The label pair probability $E_{X,w}(p,q)$ for window w may be given by:

$$E_{X,w}(p, q) = \frac{1}{D} \sum_{d=1}^{D} \frac{L_{X,w}(d, p, q)}{\sum_{p'=1}^{K} \sum_{q'=p'}^{K} L_{X,w}(d, p', q')} \quad (5)$$

Based on the label pair probability distributions $E_{X,w}$ for each window w, the inter-window HMM module 160 may build 670 an inter-window HMM 400. The transition probabilities between states in the inter-window HMM may be based on the label pair probability distributions $E_{X,w}$. Also, the inter-window HMM module may use the label pair probability distribution $E_{X,w}$ as the probability distribution of the states in window w given the SNPs in the window w. That is, the label pair distribution $E_{X,w}(p,q)$ may be used in the inter-window HMM as the probability of the state $U_{X,w,(p,q)}$ in window w given the observation (i.e., the sequence of SNPs of the input sample genotype X in the window w). Building 670 the inter-window HMM 400 for the genotype X may include determining a label probability vector $\pi_X$ a label change probability rx for the inter-window HMM.

The inter-window HMM 400 is used by the label assignment module 170 to assign 680 labels for the input sample genotype X. Assigning labels may include assigning a pair of labels for each window w of the input sample genotype X. Assigning labels may also include determining a proportion of the input sample genotype X that corresponds to each label. In some embodiments, based on the assigned labels, the input sample genotype X is phased by the phasing module 180.

Updating Annotations

Figure 7:
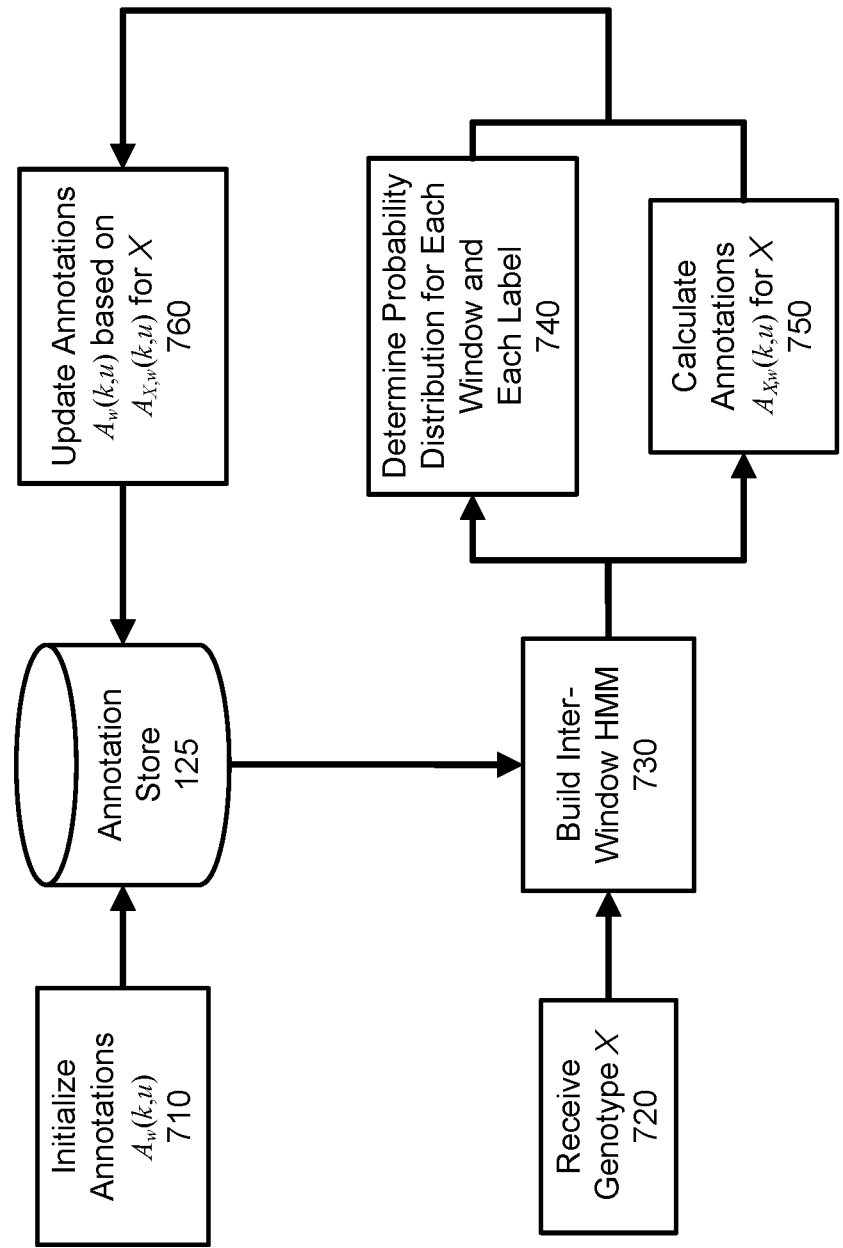
FIG. 7 is a flow diagram for assigning labels to a genotype based on a model and updating the model based on the labels assigned to the genotype, according to one embodiment.

FIG. 7 is a flow diagram for the operation of the label determination system for assigning labels to a input sample genotype X based on a model and updating the model based on the labels assigned to the input sample genotype X, according to one embodiment. By updating the model based on the labels assigned to input sample genotypes, the label determination system 100 may be iteratively improved as it processes genotypes.

The label determination system 100 initializes 710 the annotations $A_w(k,w)$ based on the set of reference panel samples $R_k$ for label k. Initializing the annotations may include performing the model training method 500 of FIG. 5. The annotations may be stored in the annotations store 125. The label determination system 100 receives 720 an input sample genotype X or accesses the input sample genotype X stored in the genotype store 130. The inter-window HMM module 160 of the label determination system 100 builds 730 an inter-window HMM 400 based on the input sample genotype X and the annotations stored in the annotation store 125.

Based on the inter-window HMM for the input sample genotype X, the label determination system 100 may determine a probability distribution $\gamma_{X,w}(k)$ for each window w and each label k. In some embodiments, the value of the probability distribution $\gamma_{X,w}(k)$ for label k may be given by:

$$\gamma_{X,w}(k) = \frac{1}{2 \times B_X(0)} \left[ \sum_{p=1}^{k} F_X(w, p, k) B_X(w, p, k) + \sum_{q=k}^{K} F_X(w, k, q) B_X(w, k, q) \right] \quad (6)$$

where $F_X$ and $B_X$ are the forward and backward functions for the inter-window HMM.

For each label k and haploid state u, learned annotations $A_{X,w}(k,u)$ may be calculated 750 for the input sample genotype X. The learned annotations $A_{X,w}(k,u)$ for input sample genotype X may be calculated in a similar manner to the annotations $A_w(k,u)$ calculated based on the reference panel samples $R_k$ when the annotations $A_w(k,u)$ were initialized 710. In some embodiments, learned annotations $A_{X,w}(k,u)$ are only calculated for a label k if the input sample genotype X has a probability distribution $\gamma_{X,w}(k)$ greater than some threshold probability. The annotation $A_{X,w}(k,u)$ may be given by:

$$A_{X,w}(k, u) = \frac{1}{b_{X,w}(\mathbb{S}_w, \mathbb{S}_w)} \sum_{v \in StatesInLevel_w} f_{X,w}(u, v) \times b_{X,w}(u, v) \quad (7)$$

After the annotations $A_{X,w}(k,u)$ for input sample genotype X are calculated 750, the annotations $A_w(k,u)$ in the annotation store 125 are updated 760 based on the newly calculated learned annotations $A_{X,w}(k,u)$ for input sample genotype X and the value of the probability distribution $\gamma_{X,w}(k)$. In some embodiments, updating the annotations $A_w(k,u)$ in the annotation store 125 includes summing the annotations based on the reference panel samples $R_k$ and the learned annotations for genotypes weighted by the value of their respective probability distributions for label k. The set of genotypes for which annotations have been calculated may be denoted by $\Phi$. The annotations based on the reference panels $R_k$ may be denoted as $A_{REF,w}(k,u)$. The reference panel annotations $A_{REF,w}(k,u)$ may have been calculated with equation 1 (or something analogous thereto) during initialization. The value of the updated annotation $A_w(k,u)$ may be given by:

$$A_w(k, u) = \frac{\theta}{\Sigma_{X \in \Phi} \gamma_{X,w}(k)} \left( \sum_{X \in \Phi} \gamma_{X,w}(k) \times A_{X,w}(k, u) \right) + (1 - \theta) A_{REF,w}(k, u) \quad (8)$$

where $\theta$ is a weighing factor ($0 \leq \theta \leq 1$) for determining the relative weight accorded to the reference panel annotations $A_{REF,w}(k,u)$ and the learned annotations $A_{X,w}(k,u)$ (for $X \in \Phi$). The weighting factor $\theta$ may increase as the number of learned annotations increases. In some embodiments, the set of genotypes $\Phi$ used to calculate the updated annotation $A_w(k,u)$ is based on the label k. For example, the set of genotypes $\Phi$ used to calculate the annotation $A_w(k,u)$ for label k may only include genotypes $X \in \Phi$ where $\gamma_{X,w}(k)$ is greater than some threshold.

In alternate embodiments, the phasing module 180 separates an input sample genotype X in the window w that has an assigned label pair $(p_{X,w}, q_{X,w})$ into two constituents haplotypes, each corresponding to a respective assigned label. The annotation $A_w(k,u)$ for a label k and a haploid state u may be based on a set $\Phi_k$, which refers to the set or a subset of the input sample genomes that were assigned to a label pair that includes k (i.e., for each $X \in \Phi_k$, $k=p_{X,w}$ or $k=q_{X,w}$). In such an embodiment, the updated annotation $A_w(k,u)$ for window w, haploid state u, and label k may be given by:

$$A_w(k, u) = \frac{\theta \, \Sigma_{X \in \Phi_k} \, \delta_{X,k}(u) \, F_X(w, p_{X,w}, q_{X,w}) B_X(w, p_{X,w}, q_{X,w})}{\Sigma_{X \in \Phi_k} \, F_X(w, p_{X,w}, q_{X,w}) B_X(w, p_{X,w}, q_{X,w})} + \\ (1 - \theta) A_{REF,w}(k, u) \quad (9)$$

where $\delta_{X,k}(u)$ is a function that is equal to 1 if the phased haplotype for genotype X corresponding to label k includes haploid state u and is equal to 0 otherwise. Alternately, $\delta_{X,k}(u)$ may be a calculation of the probability that the phased haplotype for genotype X corresponding to label k includes haploid state u.

By updating 760 the annotations for a label, based on the learned annotations $A_{X,w}(k,u)$, the accuracy of the label determination system 100 may be improved. In some embodiments, the label determination system 100 may reassign labels for a genotype X that was previously assigned labels based on earlier annotations. In such an embodiment, the label determination system 100 may use annotations $A_w$ that are not based on the learned annotations $A_{X,w}$ for input sample genotype X when assigning new labels to the input sample genotype X. For example, the set of genotypes $\Phi$ that the annotation $A_w(k,u)$ is based on excludes the input sample genotype X. After labels are determined for genotype X, the learned annotations $A_{X,w}$ for X may be updated for use in determining annotations $A_X$ used to assign labels for other genotypes.

In some embodiments, a set of genotypes is divided into batches. Each batch β is associated with annotations calculated based on the genotypes in the batch β. The batch annotations for a batch β may be based on the annotations $A_{X,w}$ for each input sample genotype X in the batch β. The annotation $A_w$ used when determining labels for a genotype X in batch β may be based on the batch annotations of the other batches, but not on the batch annotations of the batch β itself.

H may include a transition function t and a transition probability function ρ. The haploid MM H may start at a start state $\mathbb{S}_w$. The procedure by which the diploid HMM module 150 calculates the forward function $f_{G,w}$ may return the forward function $f_{G,w}$; a mapping from each level d to the set of possible diploid states for genotype G at that level d, $\alpha_{G,w}(d)$; and a mapping of each diploid state in $\alpha_{G,w}$ to the set of its possible transitions for genotype G and the corresponding transition probabilities, $\Omega_{G,w}$.

Pseudo-code for performing the forward calculation with a genotype G for a window w, according to an example embodiment, is below:

```
procedure DIPLOID-FORWARD(G, H_w, w)
    Let D_w be the number of SNPs in the window w
    Let 𝕊_w be the start state of the Markov model H_w
    Let t and ρ be the transition functions and transition probability functions for H_w
    Let α_{G,w}(d) be an initially empty list of diploid states at level d
    Let Ω_{G,w} be an initially empty mapping of diploid states to a list of possible transitions
    f_{G,w}(𝕊_w, 𝕊_w) ← 1
    Add state (𝕊_w, 𝕊_w) to α_{G,w}(0)
    for d ∈ 0, 1, 2, . . . , D_w−1 do
        Let g = G_{(S_w+d)} be the genotype at SNP d+1 of the window w.
        for each diploid state (u_1,u_2) ∈ α_{G,w}(d) do
            initialize P to an empty list of diploid states and transition likelihood
            initialize Ω_{G,w}(u_1,u_2) to an empty list of transitions and transition likelihoods
            if g is homozygous 0 then
                Add ((t(u_1,0),t(u_2,0)),ρ(u_1,0) × ρ(u_2,0)) to Ω_{G,w}(u_1,u_2)
            else if g is homozygous 1 then
                Add ((t(u_1,1),t(u_2,1)),ρ(u_1,1) × ρ(u_2,1)) to Ω_{G,w}(u_1,u_2)
            else if g is homozygous 1 then
                Add ((t(u_1,0), t(u_2,1)), 1/2 × ρ(u_1,0) × ρ(u_2,1)) to Ω_{G,w}(u_1,u_2)

Add ((t(u_1,1), t(u_2,0)), 1/2 × ρ(u_1,1) × ρ(u_2,0)) to Ω_{G,w}(u_1,u_2)

else if g is missing then
                Add ((t(u_1,0), t(u_2,0)), 1/4 × ρ(u_1,0) × ρ(u_2,0)) to Ω_{G,w}(u_1,u_2)

Add ((t(u_1,1), t(u_2,1)), 1/4 × ρ(u_1,1) × ρ(u_2,1)) to Ω_{G,w}(u_1,u_2)

Add ((t(u_1,0), t(u_2,1)), 1/4 × ρ(u_1,0) × ρ(u_2,1)) to Ω_{G,w}(u_1,u_2)

Add ((t(u_1,1), t(u_2,0)), 1/4 × ρ(u_1,1) × ρ(u_2,0)) to Ω_{G,w}(u_1,u_2)

end if
            for each ((v_1, v_2), ω) in Ω_{G,w}(u_1,u_2) do
                if (v_1,v_2) is not in α_{G,w}(d+1) then
                    initialize f_{G,w}(v_1,v_2) ← 0
                    add (v_1,v_2) to α_{G,w}(d+1)
                end if
                f_{G,w}(v_1,v_2) ← f_{G,w}(v_1,v_2) + ω× f_{G,w} (v_1,v_2)
            end for
        end for
        TRIM(α_{G,w}(d+1))
    end for
    return f_{G,w}, Ω_{G,w}, α_{G,w}
```

Forward-Backward Calculation for Diploid HMM

The diploid HMM module 150 may calculate a forward function $f_{G,w}$ for a genotype G in a window w. The diploid HMM module 150 may calculate the forward function $f_{G,w}$ based on a haploid MM $H_w$ for window w. The haploid MM This example of a DIPLOID-FORWARD procedure determines the forward probabilities in a window w for a diploid HMM based on the genotype G and the haploid MM. The procedure determines every possible transition to which the genotype G may correspond. In the example of the DIPLOID-FORWARD procedure, the transitions are stored in $\Omega_{G,w}(u_1,u_2)$, which maps a diploid state $(u_1,u_2)$ to a tuple $((v_1, v_2), \omega)$ where $(v_1,v_2)$ is the diploid state that diploid state $(u_1,u_2)$ transitions to and where w is the probability of the transition, which is based on the probabilities of the haploid transitions in the haploid MM $H_w$. Thus, the DIPLOID-FORWARD procedure builds a diploid HMM 300 for the genotype G characterized by the set of transitions $\Omega_{G,w}$ while calculating the forward function $f_{G,w}$.

This example of a DIPLOID-FORWARD procedure calculates the forward function for each diploid state $(v_1,v_2)$ at level d based on the probabilities of the diploid states at level d−1 that transition to it and the respective probabilities of those transitions. The procedure also generates a mapping $\alpha_{G,w}$ of each level d to the set of diploid states at level d to which the genotype G may possibly correspond. The TRIM $(\alpha_{G,w}(d+1))$ subroutine may remove low probability diploid states from the list of diploid states $\alpha_{G,w}(d+1)$. TRIM may remove diploid states with probabilities smaller than some threshold value, or remove probabilities up to a certain likelihood mass threshold. In some embodiments, the TRIM subroutine is omitted.

The diploid HMM module 150 may also calculate a backward function $b_{w,G}$ for a genotype G in a window w. The diploid HMM module 150 may calculate the backward function $b_{w,G}$ based on the mappings $\alpha_{G,w}$ and $\Omega_{G,w}$ generated by the procedure that calculated the forward function. Pseudo-code for performing the backward calculation with a genotype G for a window w, according to an example embodiment, is below:

```
procedure DIPLOID-BACKWARD(α_G,w, Ω_G,w, w)
    initialize b_G,w ← 0
    b_G,w(E_w, E_w) ← 1
    for d ∈ D_w − 1, D_w − 2, . . . , 2, 1, 0 do
        for each diploid state (u_1,u_2)∈ α_G,w(d)
            initialize b_G,w(u_1,u_2) ← 0
            for each ((v_1, v_2), ω) in Ω_G,w(u_1,u_2) do
                b_G,w(u_1,u_2) ← b_G,w(u_1,u_2) + b_G,w(v_1,v_2) × ω
            end for
        end for
    end for
    return b_G,w
```

The DIPLOID-BACKWARD procedure operates similarly to the DIPLOID-FORWARD procedure. The DIPLOID-BACKWARD procedure starts at the end state ($\mathbb{E}_{w,w}$) and iteratively steps through the diploid HMM built with the DIPLOID-FORWARD procedure. For a diploid state $(u_1, u_2)$, the backward function $b_{G,w}(u_1,u_2)$ is based on the based on the backwards probabilities of the diploid states that transition to the diploid state $(u_1,u_2)$. The backward function $b_{G,w}(u_1,u_2)$ is based on the product of the backward functions $b_{G,w}(v_1,v_2)$ of all the diploid states $(v_1,v_2)$ that transition to the diploid state $(u_1,u_2)$ and the respective probabilities of those transitions.

Building the Inter-Window HMM

The forward functions $F_X$ and the backwards functions $B_X$ for an inter-window HMM $M_X$ that includes W windows may be calculated by the inter-window HMM module 160. The forward and backwards functions of the start state of the inter-window HMM $M_X$ may be denoted by $F_X(0)$ and $B_X(0)$, respectively. Similarly, the forward and backwards functions of the end state of the inter-window HMM $M_X$ may be denoted by $F_X(W+1)$ and $B_X(W+1)$, respectively, and the forwards and backwards functions for a window w $(1 \le w \le W)$ and for a label pair (p,q) may be denoted by $F_X(w,p,q)$ and $B_X(w,p,q)$, respectively.

The inter-window HMM $M_X$ may include transition probabilities $P_X(U_{X,w,(p,q)},(p',q'))$ for each transition between states in the HMM $M_X$. Some of the transition probabilities $P_X(U_{X,w(p',q')},(p',q'))$ may be based on a label probability vector $\pi_X$. The inter-window HMM $M_X$ may also include the label pair probability distribution $E_{X,w}$. Each label pair probability $E_{X,w}(p,q)$ may be the probability of the state $U_{X,w,(p,q)}$ given the observation of window w.

Pseudo-code for performing the forward-backward calculation, according to an example embodiment, is below:

procedure INTER-WINDOW_FORWARD-BACKWARD($M_X$)
  for $1 \le p \le q \le K$:
    $F_X(0) = 1$
    $F_X(1, p, q) = \pi_{X,(p,q)} \times E_{X,1}(p, q)$
  end for
  for $2 \le w \le W$ and for $1 \le p \le q \le K$:

$$F_X(w, p, q) = E_{X,w}(p, q) \sum_{p'=1}^{K} \sum_{q'=p'}^{K} F_X(w-1, p', q') \times P_X(U_{X,w-1,(p',q')}, (p, q))$$

end for $$F_X(W+1) = \sum_{p'=1}^{K} \sum_{q'=p'}^{K} F_X(W, p', q')$$

for $1 \le p \le q \le K$:
    $B_X(W, p, q) = 1$
  end for
  $B_X(W+1) = 1$
  for $W - 1 \le w \le 1$ and for $1 \le p \le q \le K$:

$$B_X(w, p, q) = \sum_{p'=1}^{K} \sum_{q'=p'}^{K} B_X(w+1, p', q') \times P_X(U_{X,w,(p,q)}, (p', q')) \times E_{X,w+1}(p', q')$$

end for
  for $1 \le p \le q \le K$:

-continued $$B_X(0) = \sum_{p'=1}^{K} \sum_{q'=p'}^{K} \pi_{X,(p',q')} \times E_{X,1}(p', q') \times B_X(1, p', q')$$

end for
return $F_X$, $B_X$

The inter-window HMM module 160 may build an inter-window HMM $M_X$ for a input sample genotype X. Building the inter-window HMM $M_X$ may include calculating a label probability vector $\pi_X$ and the label change probability $\tau_X$. The label probability vector $\pi_X$ may be initialized to a uniform distribution (i.e., $\pi_{X,(p,q)}=1/T$ for all p and q where T=K×(K+1)/2). In some embodiments, because each unordered pair of labels with different labels corresponds to two ordered pairs while each unordered pair of the same label corresponds to a single ordered pair, the label probability vector $\pi_X$ is initialized to $\pi_{X,(p,q)}=2/K^2$ for all values of p and q where p≠q and $\pi_{X,(p,p)}=1/K^2$ for all p. The label probability vector $\pi_X$ may be iteratively updated with expectation-maximization (e.g., with the Baum-Welch algorithm). In some embodiments, the inter-window HMM module may perform N iterations of the Baum-Welch algorithm to calculate the label probability vector $\pi_X$. The label change probability $\tau_X$ may be initialized to a low value (e.g., between 0.5 to $10^{-4}$) and iteratively updated. Pseudo-code for building the inter-window HMM $M_X$, according to an example embodiment, is below:

```
procedure BUILD_INTER-WINDOW_HMM(E_{X,w})
    initialize the inter-window HMM M_x
        where the label probability vector of M_X is π_X,
        where the label change probability of M_X is τ_X, and
        where the emission probabilities of M_X is E_{X,w}
```

$$T = \frac{K(K+1)}{2}$$

for $1 \le p \le q \le K$:

$$\pi_{X,(p,q)} \leftarrow \frac{1}{T}$$

end for
$\tau = 10^{-3}$
repeat (N)
    $(F_X, B_X)$ = INTER-WINDOW_FORWARD-BACKWARD($M_x$)
    for $1 \le p \le q \le K$:

$$E[\pi_{X(p,q)}] \leftarrow \sum_{w=1}^{W} F_X(w, p, q) \times B_X(w, p, q)$$

end for
for $1 \le p \le q \le K$:

$$\pi_{X,(p,q)} \leftarrow \frac{E[\pi_{X,(p,q)}]}{\sum_{p'=1}^{K} \sum_{q'=p'}^{K} E[\pi_{X,(p',q')}]}$$

end for $$\sigma \leftarrow \sum_{w=1}^{W} \sum_{1 \le p \le q \le K} F_X(w, p, q) \sum_{1 \le p' \le q' \le K} P_X(U_{X,w,(p,q)}, (p', q')) \times B_X(w+1, p', q')$$

$$\tau_X \leftarrow 1 - \frac{1}{\sigma} \sum_{w=1}^{W} \sum_{p=1}^{K} \sum_{q=p}^{K} F_X(w, p, q) \times P_X(U_{X,w,(p,q)}, (p, q)) \times B_X(w+1, p, q)$$

end repeat loop
return $M_x$

In the example BUILD_INTER-WINDOW_HMM procedure, the label pair expectation $E[\pi_{X,(p,q)}]$ is calculated for each of the pair of labels (p,q). The label pair expectation $E[\pi_{X,(p,q)}]$ is the sum of the probabilities of each state $U_{X,w,(p,q)}$ for each window w and is therefore equal to the expected number of windows w that have a hidden state $U_{X,w,(p,q)}$ corresponding to the label pair (p,q). Each label probability $\pi_{X,(p,q)}$ is updated to a new value: the label pair expectation $E[\pi_{X,(p,q)}]$ of the label pair (p,q) divided by the sum of label pair expectations for all label pair probabilities, so that the label probabilities $\pi_{X,(p,q)}$ sum to unity (i.e., $\Sigma \pi_X = 1$).

In the example BUILD_INTER-WINDOW_HMM procedure, the label change probability $\tau_X$ is initialized to $10^{-3}$ and then iteratively updated to the expected number of transitions that do not change label assignments. That is, the label change probability $\tau_X$ is updated to the complement of the expected number of transitions between states that correspond to the same labels (i.e., the expected number of transitions from a state $U_{X,w+1,(p,q)}$ to a state $U_{X,w+1,(p,q)}$) divided by the expected number of all transitions between states. In the example BUILD_INTER-WINDOW_HMM procedure, the expected number of all transitions between states is represented as σ.

Additional Considerations

The label determination system 100 is implemented using one or more computers having one or more processors executing application code to perform the steps described herein, and data may be stored on any conventional non-transitory storage medium and, where appropriate, include a conventional database server implementation. For purposes of clarity and because they are well known to those of skill in the art, various components of a computer system, for example, processors, memory, input devices, network devices and the like are not shown in FIG. 1. In some embodiments, a distributed computing architecture is used to implement the described features. One example of such a distributed computing platform is the Apache Hadoop project available from the Apache Software Foundation.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

The algorithms and displays presented are not inherently related to any particular computer or other apparatus. Various general-purpose systems may also be used with programs in accordance with the teachings above, or it may prove convenient to construct more specialized apparatus to perform the required method steps. The required structure for a variety of these systems will appear from the description above. In addition, a variety of programming languages may be used to implement the teachings above.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

What is claimed is:

1. A computer-implemented method comprising:
accessing an input sample genetic dataset of an individual;
dividing the input sample genetic dataset into a plurality of windows, each window comprising a set of a plurality of single nucleotide polymorphisms (SNPs);
generating, using the divided input sample genetic dataset, an inter-window hidden Markov model (HMM), wherein the inter-window HMM comprises:
  (i) for each window, a set of nodes representing the window, each node in the set corresponding to a pair of labels and associated with an emission probability, each label in the pair representing an ethnicity label for the plurality of SNPs included in the window;
  (ii) a plurality of edges, each edge connecting a first node of a first set of nodes representing a first window to a second node of a second set of nodes representing a second window, each edge representing a transition from the first node to the second node;
and wherein the inter-window HMM is trained by:
  receiving haplotype data corresponding to sequences of alleles of individuals;
  building per-window models for the plurality of windows;
  receiving a set of reference panel samples; and
  training the per-window models using the set of reference panel samples to generate the emission probability for each node of each window in the inter-window HMM; and
assigning one or more ethnicity labels to the input sample genetic dataset using the inter-window HMM.

2. The method of claim 1, wherein the emission probability associated with at least one of the nodes in one of the windows is proportional to the probability of the individual having the set of SNPs in the one of the windows given the pair of labels of the node.

3. The method of claim 1, wherein assigning the one or more ethnicity labels to the input sample genetic dataset comprises one or more of the following: calculating a Viterbi path for the inter-window HMM, calculating a plurality of stochastic paths calculated for the inter-window HMM, and determining, for each of the one or more ethnicity labels, a proportion of the input sample genetic dataset that corresponds to the ethnicity label.

4. The method of claim 1, wherein assigning the one or more ethnicity labels to the input sample genetic dataset comprises:
accessing a second sample genetic dataset;
determining one or more overlapping genetic regions between the input sample genetic dataset and the second sample genetic dataset; and
assigning the one or more ethnicity labels for the one or more overlapping genetic regions.

5. The method of claim 1, wherein at least one edge of the plurality of edges is associated with a transition probability, the transition probability indicating a likelihood that the first node of the first set of nodes representing the first window will transition to the second node of the second set of nodes representing the second window.

6. The method of claim 1, wherein each ethnicity label corresponds to an ethnic group.

7. The method of claim 1, further comprising calculating a label probability vector for each window of the inter-window HMM based on a distribution of the emission probabilities of the window, wherein the plurality of edges of the inter-window HMM are based on the label probability vectors.

8. The method of claim 1, further comprising calculating a label change probability for the inter-window HMM based on the emission probabilities, the label change probability indicating a likelihood that two sequential nodes in sequential windows do not correspond to the same pair of labels given that the sequential windows correspond to a same chromosome.

9. A non-transitory computer-readable storage medium storing executable computer program instructions, the computer program instructions, when executed by one or more computer processors, cause the one or more computer processors to perform steps comprising:
accessing an input sample genetic dataset of an individual;
dividing the input sample genetic dataset into a plurality of windows, each window comprising a set of a plurality of single nucleotide polymorphisms (SNPs);
generating, using the divided input sample genetic dataset, an inter-window hidden Markov model (HMM), wherein the inter-window HMM comprises:
(i) for each window, a set of nodes representing the window, each node in the set corresponding to a pair of labels and associated with an emission probability, each label in the pair representing an ethnicity label for the plurality of SNPs included in the window;
(ii) a plurality of edges, each edge connecting a first node of a first set of nodes representing a first window to a second node of a second set of nodes representing a second window, each edge representing a transition from the first node to the second node;
and wherein the inter-window HMM is trained by:
receiving haplotype data corresponding to sequences of alleles of individuals;
building per-window models for the plurality of windows;
receiving a set of reference panel samples; and
training the per-window models using the set of reference panel samples to generate the emission probability for each node of each window in the inter-window HMM; and
assigning one or more ethnicity labels to the input sample genetic dataset using the inter-window HMM.

10. The computer-readable storage medium of claim 9, wherein the emission probability associated with at least one of the nodes in one of the windows is proportional to the probability of the individual having the set of SNPs in the one of the windows given the pair of labels of the node.

11. The computer-readable storage medium of claim 9, wherein assigning the one or more ethnicity labels to the input sample genetic dataset comprises one or more of the following: calculating a Viterbi path for the inter-window HMM, calculating a plurality of stochastic paths calculated for the inter-window HMM, and determining, for each of the one or more ethnicity labels, a proportion of the input sample genetic dataset that corresponds to the ethnicity label.

12. The computer-readable storage medium of claim 9, wherein at least one edge of the plurality of edges is associated with a transition probability, the transition probability indicating a likelihood that the first node of the first set of nodes representing the first window will transition to the second node of the second set of nodes representing the second window.

13. The computer-readable storage medium of claim 9, wherein assigning the one or more ethnicity labels to the input sample genetic dataset comprises:
accessing a second sample genetic dataset;
determining one or more overlapping genetic regions between the input sample genetic dataset and the second sample genetic dataset; and
assigning the one or more ethnicity labels for the one or more overlapping genetic regions.

14. The computer-readable storage medium of claim 9, wherein each ethnicity label corresponds to an ethnic group.

15. The computer-readable storage medium of claim 9, further comprising calculating a label probability vector for each window of the inter-window HMM based on a distribution of the emission probabilities of the window, wherein the plurality of edges of the inter-window HMM are based on the label probability vectors.

16. The computer-readable storage medium of claim 9, further comprising calculating a label change probability for the inter-window HMM based on the emission probabilities, the label change probability indicating a likelihood that two sequential nodes in sequential windows do not correspond to the same pair of labels given that the sequential windows correspond to a same chromosome.

17. A system comprising:
one or more computer processors; and
memory storing executable computer program instructions, the computer program instructions, when executed by the one or more computer processors, cause the one or more computer processors to perform steps comprising:
accessing an input sample genetic dataset of an individual;
dividing the input sample genetic dataset into a plurality of windows, each window comprising a set of a plurality of single nucleotide polymorphisms (SNPs);
generating, using the divided input sample genetic dataset, an inter-window hidden Markov model (HMM), wherein the inter-window HMM comprises:
(i) for each window, a set of nodes representing the window, each node in the set corresponding to a pair of labels and associated with an emission probability, each label in the pair representing an ethnicity label for the plurality of SNPs included in the window;

(ii) a plurality of edges, each edge connecting a first node of a first set of nodes representing a first window to a second node of a second set of nodes representing a second window, each edge representing a transition from the first node to the second node;

and wherein the inter-window HMM is trained by:
receiving haplotype data corresponding to sequences of alleles of individuals;
building per-window models for the plurality of windows;
receiving a set of reference panel samples; and
training the per-window models using the set of reference panel samples to generate the emission probability for each node of each window in the inter-window HMM; and assigning one or more ethnicity labels to the input sample genetic dataset using the inter-window HMM.

18. The system of claim 17, wherein assigning the one or more ethnicity labels to the input sample genetic dataset comprises:
accessing a second sample genetic dataset;
determining one or more overlapping genetic regions between the input sample genetic dataset and the second sample genetic dataset; and
assigning the one or more ethnicity labels for the one or more overlapping genetic regions.

19. The system of claim 17, wherein the emission probability associated with at least one of the nodes in one of the windows is proportional to the probability of the individual having the set of SNPs in the one of the windows given the pair of labels of the node.

20. The system of claim 17, further comprising instructions for calculating a label change probability for the inter-window HMM based on the emission probabilities, the label change probability indicating a likelihood that two sequential nodes in sequential windows do not correspond to the same pair of labels given that the sequential windows correspond to a same chromosome.

* * * * *